United States Patent
Jain et al.

(10) Patent No.: US 11,158,423 B2
(45) Date of Patent: Oct. 26, 2021

(54) ADAPTED DIGITAL THERAPEUTIC PLANS BASED ON BIOMARKERS

(71) Applicant: VIGNET INCORPORATED, Fairfax, VA (US)

(72) Inventors: Praduman Jain, Fairfax, VA (US); Josh Schilling, Salem, OR (US); Dave Klein, Oakton, VA (US); Neeta Jain, Fairfax, VA (US); Yue Cao, Vienna, VA (US)

(73) Assignee: VigNet Incorporated, Fairfax, VA (US)

( * ) Notice: Subject to any disclaimer, the term of this patent is extended or adjusted under 35 U.S.C. 154(b) by 6 days.

(21) Appl. No.: 16/172,346

(22) Filed: Oct. 26, 2018

(65) Prior Publication Data

US 2020/0131581 A1 Apr. 30, 2020

(51) Int. Cl.
| | |
|---|---|
| *G16H 40/67* | (2018.01) |
| *G16H 50/20* | (2018.01) |
| *G16H 50/30* | (2018.01) |
| *G16H 10/60* | (2018.01) |

(Continued)

(52) U.S. Cl.
CPC ............. *G16H 40/67* (2018.01); *G16H 10/60* (2018.01); *G16H 15/00* (2018.01); *G16H 50/20* (2018.01); *G16H 50/30* (2018.01); *G16H 80/00* (2018.01)

(58) Field of Classification Search
None
See application file for complete search history.

(56) References Cited

U.S. PATENT DOCUMENTS

| | | |
|---|---|---|
| 6,039,688 A | 3/2000 | Douglas et al. |
| 6,260,022 B1 | 7/2001 | Brown |
| 6,269,339 B1 | 7/2001 | Silver |

(Continued)

FOREIGN PATENT DOCUMENTS

| | | |
|---|---|---|
| EP | 2545468 | 3/1951 |
| WO | WO 2011112556 | 9/2011 |

(Continued)

OTHER PUBLICATIONS

U.S. Appl. No. 15/803,556, filed Nov. 3, 2017, Jain et al.

(Continued)

*Primary Examiner* — Olivia M. Wise
(74) *Attorney, Agent, or Firm* — Fish & Richardson P.C.

(57) ABSTRACT

A system and method for an adjustable bio-stream self-selecting system. Through a plethora of inputs, the system associates therapeutic recipes and associated biomarker in a personalized approach to recommending an individual to a specific therapeutic program. Therapeutic programs operate in accordance with personalized inputs suggested by the user and through digital markers and biomarkers, which trigger new recommendations by "knowing" the individual. Each bio-stream contains information utilized within these bio-markers to trigger additional therapy recommendations. Because of the complexity of the plurality of inputs, these biomarkers are managed in a way that enables low latency detections, low bandwidth needs, low processing needs, and less battery needs. The pre-processing of these biomarkers helps additional therapy management and precision medicine across larger global population needs of the system.

31 Claims, 14 Drawing Sheets

(51) Int. Cl.
    *G16H 80/00*     (2018.01)
    *G16H 15/00*     (2018.01)

(56) References Cited

U.S. PATENT DOCUMENTS

| | | |
|---|---|---|
| 7,076,534 B1 | 7/2006 | Cleron et al. |
| 7,330,717 B2 | 2/2008 | Gidron et al. |
| 7,447,643 B1 | 11/2008 | Olson et al. |
| 7,730,063 B2 | 6/2010 | Eder |
| 7,935,613 B2 | 5/2011 | Gizewski |
| 8,347,263 B1 | 1/2013 | Offer |
| 8,997,038 B2 | 3/2015 | Becker |
| 9,134,964 B2 | 9/2015 | Hirsch |
| 9,170,800 B2 | 10/2015 | Lang |
| 9,361,011 B1 | 6/2016 | Burns |
| 9,426,433 B1 | 8/2016 | Mazzarella |
| 9,461,972 B1 | 10/2016 | Mehta |
| 9,715,370 B2 | 7/2017 | Friedman |
| 9,753,618 B1 | 9/2017 | Jain |
| 9,844,725 B1 | 12/2017 | Durkin et al. |
| 9,848,061 B1 | 12/2017 | Jain et al. |
| 9,858,063 B2 | 1/2018 | Jain et al. |
| 1,020,576 A1 | 2/2019 | Sehgal |
| 1,052,155 A1 | 12/2019 | Jain |
| 2001/0019338 A1 | 9/2001 | Roth |
| 2002/0010596 A1 | 1/2002 | Matory |
| 2002/0022973 A1 | 2/2002 | Sun |
| 2002/0157091 A1 | 10/2002 | DeMello et al. |
| 2003/0078960 A1 | 4/2003 | Murren et al. |
| 2003/0165954 A1 | 9/2003 | Katagiri et al. |
| 2003/0182429 A1 | 9/2003 | Jagels |
| 2003/0229522 A1 | 12/2003 | Thompson et al. |
| 2004/0030424 A1 | 2/2004 | Corl |
| 2004/0203755 A1 | 10/2004 | Brunet et al. |
| 2005/0050320 A1 | 3/2005 | Wassmann et al. |
| 2005/0086587 A1 | 4/2005 | Balz |
| 2005/0144072 A1 | 6/2005 | Perkowski et al. |
| 2005/0186550 A1 | 8/2005 | Gillani |
| 2005/0246304 A1 | 11/2005 | Knight et al. |
| 2006/0041452 A1 | 2/2006 | Kulkarni |
| 2006/0107219 A1 | 5/2006 | Ahya |
| 2006/0205564 A1 | 9/2006 | Peterson |
| 2006/0282516 A1 | 12/2006 | Taylor |
| 2007/0021984 A1 | 1/2007 | Brown |
| 2007/0172844 A1 | 7/2007 | Lancaster et al. |
| 2007/0231828 A1 | 10/2007 | Beachy et al. |
| 2007/0259351 A1 | 11/2007 | Chinitz et al. |
| 2007/0281285 A1 | 12/2007 | Jayaweera |
| 2008/0005679 A1 | 1/2008 | Rimas-Ribikauskas |
| 2008/0034314 A1 | 2/2008 | Louch et al. |
| 2008/0046038 A1* | 2/2008 | Hill ............... A61B 5/0031 607/60 |
| 2008/0126110 A1 | 5/2008 | Haeberle |
| 2008/0127040 A1 | 5/2008 | Barcellona |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0311968 A1 | 12/2008 | Hunter |
| 2009/0023555 A1 | 1/2009 | Raymond |
| 2009/0024944 A1 | 1/2009 | Louch |
| 2009/0031215 A1 | 1/2009 | Collier |
| 2009/0035733 A1 | 2/2009 | Meitar |
| 2009/0043689 A1 | 2/2009 | Yang |
| 2009/0076856 A1 | 3/2009 | Darby et al. |
| 2009/0119678 A1 | 5/2009 | Shih |
| 2009/0125333 A1 | 5/2009 | Heywood |
| 2009/0156190 A1 | 6/2009 | Fisher |
| 2009/0163182 A1 | 6/2009 | Gatti |
| 2009/0170715 A1 | 7/2009 | Glinsky |
| 2009/0172002 A1 | 7/2009 | Bathiche |
| 2009/0248883 A1 | 10/2009 | Suryanarayana et al. |
| 2009/0276771 A1 | 11/2009 | Nickolov et al. |
| 2010/0041378 A1 | 2/2010 | Aceves |
| 2010/0082367 A1 | 4/2010 | Hains et al. |
| 2010/0179833 A1 | 7/2010 | Roizen et al. |
| 2010/0211941 A1 | 8/2010 | Roseborough |
| 2010/0250341 A1 | 9/2010 | Hauser |
| 2010/0262664 A1 | 10/2010 | Brown et al. |
| 2011/0184748 A1 | 7/2011 | Fierro et al. |
| 2011/0200979 A1 | 8/2011 | Benson et al. |
| 2011/0230360 A1 | 9/2011 | Stephan et al. |
| 2012/0084399 A1 | 4/2012 | Scharber et al. |
| 2012/0102050 A1 | 4/2012 | Button |
| 2012/0220835 A1 | 8/2012 | Chung |
| 2012/0272156 A1 | 10/2012 | Kerger |
| 2013/0103749 A1 | 4/2013 | Werth et al. |
| 2013/0110565 A1 | 5/2013 | Means |
| 2013/0166494 A1 | 6/2013 | Davis et al. |
| 2013/0238686 A1 | 9/2013 | O'Donoghue |
| 2013/0283188 A1 | 10/2013 | Sanghvi |
| 2013/0329632 A1 | 12/2013 | Buyukkoc et al. |
| 2014/0019191 A1 | 1/2014 | Mulji |
| 2014/0026113 A1 | 1/2014 | Farooqi |
| 2014/0033171 A1 | 1/2014 | Lorenz |
| 2014/0058755 A1 | 2/2014 | Macoviak et al. |
| 2014/0088995 A1 | 3/2014 | Damani |
| 2014/0100883 A1 | 4/2014 | Hamilton |
| 2014/0101628 A1 | 4/2014 | Almog |
| 2014/0109072 A1 | 4/2014 | Lang et al. |
| 2014/0109115 A1 | 4/2014 | Low |
| 2014/0109177 A1 | 4/2014 | Barton et al. |
| 2014/0156823 A1 | 6/2014 | Liu |
| 2014/0181715 A1 | 6/2014 | Axelrod |
| 2014/0187228 A1 | 7/2014 | Fisher |
| 2014/0240122 A1 | 8/2014 | Roberts |
| 2014/0257058 A1 | 9/2014 | Clarysse et al. |
| 2014/0257852 A1 | 9/2014 | Walker et al. |
| 2014/0273913 A1 | 9/2014 | Michel |
| 2014/0278536 A1 | 9/2014 | Zhang |
| 2014/0297311 A1 | 10/2014 | Jackson |
| 2014/0358482 A1 | 12/2014 | Sehgal |
| 2014/0365961 A1 | 12/2014 | Lefor et al. |
| 2015/0019342 A1 | 1/2015 | Gupta |
| 2015/0025917 A1 | 1/2015 | Stempora |
| 2015/0025997 A1 | 1/2015 | Tilenius et al. |
| 2015/0056589 A1 | 2/2015 | Zhang et al. |
| 2015/0074635 A1 | 3/2015 | Margiotta |
| 2015/0089224 A1 | 3/2015 | Beckman |
| 2015/0135160 A1 | 5/2015 | Gauvin |
| 2015/0143470 A1 | 5/2015 | Stiekes et al. |
| 2015/0148061 A1 | 5/2015 | Koukoumidis |
| 2015/0163121 A1 | 6/2015 | Mahaffey |
| 2015/0199490 A1 | 7/2015 | Iancu et al. |
| 2015/0294090 A1 | 10/2015 | Kodiyan |
| 2015/0356701 A1 | 12/2015 | Gandy |
| 2016/0058287 A1 | 3/2016 | Dyell |
| 2016/0086297 A1* | 3/2016 | Dettinger ............ G06Q 10/101 705/3 |
| 2016/0092339 A1 | 3/2016 | Straub |
| 2016/0189317 A1 | 6/2016 | Papandrea |
| 2017/0011200 A1 | 1/2017 | Arshad et al. |
| 2017/0020444 A1 | 1/2017 | Lurie |
| 2017/0048215 A1 | 2/2017 | Straub |
| 2017/0124276 A1 | 5/2017 | Tee |
| 2017/0132395 A1 | 5/2017 | Futch |
| 2017/0303187 A1 | 10/2017 | Crouthamel et al. |
| 2017/0329483 A1 | 11/2017 | Jann et al. |
| 2017/0329500 A1 | 11/2017 | Grammatikakis et al. |
| 2017/0330297 A1 | 11/2017 | Cronin et al. |
| 2017/0344895 A1 | 11/2017 | Roy |
| 2017/0374178 A1 | 12/2017 | Sharma et al. |
| 2018/0121187 A1 | 5/2018 | Jain et al. |
| 2018/0197624 A1 | 7/2018 | Robaina et al. |
| 2018/0232492 A1* | 8/2018 | Al-Alul ............... G06F 19/325 |
| 2018/0308569 A1 | 10/2018 | Luellen |
| 2019/0019581 A1 | 1/2019 | Vaughan et al. |
| 2019/0043501 A1 | 2/2019 | Ramaci |
| 2019/0043610 A1 | 2/2019 | Vaughan |
| 2019/0043619 A1 | 2/2019 | Vaughan et al. |
| 2019/0074080 A1 | 3/2019 | Appelbaum et al. |
| 2019/0172588 A1 | 6/2019 | Tran et al. |
| 2019/0180862 A1 | 6/2019 | Wisser et al. |
| 2019/0207814 A1 | 7/2019 | Jain et al. |

(56) References Cited

U.S. PATENT DOCUMENTS

| | | |
|---|---|---|
| 2019/0214116 A1 | 7/2019 | Eberting |
| 2019/0243944 A1 | 8/2019 | Jain et al. |
| 2019/0286086 A1 | 9/2019 | Gardner et al. |
| 2019/0313934 A1 | 10/2019 | Lee et al. |
| 2019/0320310 A1 | 10/2019 | Horelik et al. |
| 2020/0019995 A1 | 1/2020 | Krishnan et al. |
| 2020/0050330 A1 | 2/2020 | Schilling et al. |
| 2020/0112479 A1 | 4/2020 | Jain et al. |
| 2020/0119986 A1 | 4/2020 | Jain et al. |

FOREIGN PATENT DOCUMENTS

| | | |
|---|---|---|
| WO | WO 2012078753 | 6/2012 |
| WO | WO 2016161416 | 10/2016 |
| WO | WO 2017106770 | 6/2017 |

OTHER PUBLICATIONS

[No Author Listed] "Cancer Care Patient Navigation. A practical guide for community cancer centers," Association of Community Cancer Centers, 2009, [retrieved on Jan. 2, 2018], retrieved from: URL <https://www.accc-cancer.org/resources/pdf/Patient-Navigation-Guide.pdf>, 40 pages.

[No Author Listed] "Digital therapeutics," Wikipedia, Nov. 20, 2017, [retrievedon Jan. 2, 2018], retrieved from: URL <https://en.wikipedia.org/wiki/Digital_therapeutics>, 4 pages.

[No Author] "Methods for JIAIs Just in Time Adaptive Intervention," 2016, Nov. 9, 2016, [retreieved on Nov. 9, 2016], from the internet <https://community.isr.umich.edu/public/Default.aspx?alias=community.isr.umich.edu/public/jitai&>.

Airwatch: "AirWatch Enterprise Mobility Management Demo," YouTube, Jul. 22, 2014, retrieved on May 3, 2017, retrieved from URL <https://www.youtube.com/watch?v=ucV1n4-tgk>, 1 page.

Airwatch: "Airwatch Laptop Management Demo," YouTube, Oct. 3, 2014, retrieved on May 3, 2017, retrieved from URL<https://www.youtube.com/watch?v=3gHfmdVZECM>, 1 page.

Braun et al., "Cancer Patient Navigator Tasks across the Cancer Care Continuum," J Health Care Poor Underserved, Feb. 1, 2012, 23(1):398-413.

Conner, "Experience sampling and ecological momentary assessment with mobile phones," 2015—http://www.otago.ac.nz/psychology/otago047475.pdf.

Farr, "Can "Digital Therapeutics" Be as Good as Drugs?," MIT Technology Review, Apr. 7, 2017, [retrieved on Jan. 2, 2018], retrieved from: URL <https://www.technologyreview.com/s/604053/can-digital-therapeutics-be-as-good-as-drugs/>, 8 pages.

Guyot, "Apple's ResearchKit: Our Complete Overview," Mar. 9, 2015, retrieved on Mar. 30, 2020, retrieved from URL<https://www.macstories.net/news/apples-researchkit-our-complete-overview/>, 8 pages.

Henze et al., "Push the study to the App store: evaluating off-screen visualizations for maps in the android market," Proceedings of the 12th Conference on Human-Computer Interaction with Mobile Devices and Services, Lisbon, Portugal, Sep. 7-10, 2010, 373-374.

Heron, "Ecological Momentary Intervention [EMI]: Incorporating mobile technology into a disordered eating treatment program for college women," Psychology—Dissertations, paper 157, 2011.

http://www.khanacademic.org, [online], "Khan Academy," May 12, 2017, retrieved on Jan. 2, 2018, retrieved from URL <Khanacademic.org>, 1 page.

Lunn et al., "Using Mobile Technology to Engage Sexual and Gender Minorities in Clinical Research," PLOS ONE, May 2, 2019, 14(5), 19 pages.

Matthews, "Johns Hopkins Researchers to Use Apple Watch Data to Study Epilepsy," Oct. 15, 2015, retrieved on Mar. 30, 2020, retrieved from URL<https://hub.jhu.edu/2015/10/15/apple-watch-epiwatch/>, 3 pages.

Milward, "Ecological momentary assessment," Jul. 2015, [retrieved on May 12, 2017], from the internet <https://www.addiction-ssa.org/commentary/emerging-research-methods-series-ecological-momentary-assessment>, 3 pages.

Pogue, "Apple's First 5 Health ResearchKit Apps in Brief," Jul. 1, 2015, retreived on Mar. 30, 2020, retrieved from URL<https://www.scientificamerican.com/article/pogue-apples-first-5-health-researchkit-apps-in-brief/>, 4 pages.

Runyan et al., "Virtues, ecological momentary assessment/intervention and smartphone technology," Front Psychol, 2015;6:481.

Shockney, "The Value of Patient Navigators as Members of the Multidisciplinary Oncology Care Team," 2017 ASCO Annual Meeting, ASCO Daily News, Jun. 6, 2016, [retrieved on Jan. 2, 2018], retrieved from: URL <https://am.asco.org/value-patient-navigators-members-multidisciplinary-oncology-care-team>, 3 pages.

Simon, "Patient Navigators Help Cancer Patients Manage Care," American Cancer Society, Feb. 24, 2017, [retrieved on Jan. 2, 2018], retrieved from: URL <https://www.cancer.org/latest-news/navigators-help-cancer-patients-manage-their-care.html>, 4 pages.

Taivan et al., "Application Diversity in Open Display Networks," Proceedings of the International Symposium on Pervasive Displays, Copenhagen, Denmark, Jun. 2014, 68-73.

Teems, "Automated Patient Navigation: Commission on Cancer and Other Requirements," Cordata Healthcare Innovations; Cordata Blog, Oct. 13, 2014, [retrieved on Jan. 2, 2018], retrieved from: URL <http://www.cordatahealth.com/blog/automated-patient-navigation-commission-on-cancer-and-other-requirements>, 4 pages.

Tourous et al., "Empowering the Digital Therapeutic Relationship: Virtual Clinics for Digital Health Interventions," NPJ Digital Medicine, May 2018, 1(16):1-3.

* cited by examiner

FIG. 4 — 125

Therapeutic Engagement Post-processing Determination (Biomarker Validation) — Behavioral Cases — 133

| Anxiety | Attention Deficit | Boredom | Depression | Disrupted Sleeping | Fatigue |
|---|---|---|---|---|---|
| Loneliness | Loss Of Appetite | Mental Health | Social Avoidance | Stress | Work/life Balance |

Biomarker Predictors Pre-Processing Tags — Feature Classification — 131

| User Is Actively Checking Phone | User Biomarkers Are Changing | Phone Intensely Being Utilized | User Is Watching Television | User Is Sleeping | User Is Eating |
|---|---|---|---|---|---|
| User Is Actively Using An App | Environment Has A Sudden Change | User Is Showing Interest | User Hasn't Moved | User Is Commuting | User Is Engaged In Conversation |
| User Is Rapidly Changing Apps | User Is Pacing | User Is Avoiding | Typing Accuracy Decreased | User Is Sleeping Well | User Is Actively Moving |
| Fidget Spinning | Battery Is Rapidly Depleting | Social Proximity Is Increasing | User Is Shaking | Sleeping May Be Interrupted | Weather May Be Mood Altering |

Sensors Classifiers — Sensor Types — 129

| Audio | Networking | Phone | Environment | Positioning & Activity | User Storage & Interactions |
|---|---|---|---|---|---|

Sensors/Drivers — Sensors — 127

| Raw Audio | Bluetooth State | App Class | Barometer | Accelerometer | Keyboard |
|---|---|---|---|---|---|
| Audio Noise Classifiers | Bluetooth Nearby Devices | App Name | Camera Image Detection | Altimeter | Screen |
| Audio Transcripts | Network State | App Usage | Camera Light Wavelength | GPS | Touch |
| Ambient Sound Level | Telephony State | App State | Ambient Light Levels | Gravity | Touch Patterns |
| Microphone State | Wi-Fi State | Battery Level | Proximity | Gyroscope | User Health Storage |
| Speaker Levels | Wi-Fi Nearby Ap | Battery State | Temperature | Linear Accelerometer | Time Zone |
| Speaker Control Adjustments | Call Log | SMS Content | Processor Usage | Location Classification | Magnetometer |
| Audio Filtering | Phone Usage | SMS Log | Semantic Time | User Acceleration | Rotation |

| Therapy Recipe Plans For Cancer Survivorship | Cancer Survivorship Therapy Recipe 1- Depression | Cancer Survivorship Therapy Recipe 2- Fatigue | Cancer Survivorship Therapy Recipe 3- Pain |
|---|---|---|---|
| Personalization Question 1- | How Many Hours Do You Sleep Each Night? | How Many Steps Do You Get On An Average Day? Or Minutes Do You Walk, Run Or Exercise? | Are You Currently Sick Or Tired At All? Can You Talk For A Little Bit, That Will Give A Sense Of Your Speech For Our Expression Recognition To Help Detect Changes In Your Voice And Face. |
| Personalization Question 2- | How Often Do You Go To A Public Location? And For How Long During That Time Is Spent At That Location? | Lets Test Your Cognitive Responsiveness With A Short Game Would You Say Your Cognitive Levels Are As Good As Any Other Day Or Are They Heightened Or Diminished In Anyway? | Lets Try Walking In A Straight Line Now, Can You Walk For 2 Minutes In A Circle Clockwise? Now Counterclockwise? And Now A Steps In A Forward Straight Motion? |
| Personalization Question 3- | How Often In An Average Day Or Week Do You Use Substances Like Alcohol Or Opioids Or Other Substances? | Do You Get A Full Night Of Rested Sleep? How Many Times Do You Wake Up During Your Rest? | When Your Pain Is At Its Lowest - How Often Do You Adjust Yourself When Sitting In A Chair? Do You Toss And Turn While Sleeping? |
| Personalized Plan- | Get Out Of Bed After 8 Hours Regardless Of Sleep, Go To A Public Place Once A Day, Limit Substances Or Avoid If Dependencies Exist. | Get Active Every Hour While Not In Bed, Score Above Average Results On Short Cognitive Game Throughout The Day At Least Morning And Evening, Try To Get Continuous Sleep When Sleeping. | Vocal/face Check-in Once A Day, Consistent Gait Throughout The Day, Comfortable Sitting And Sleeping. |

FIG. 5A

| | | | |
|---|---|---|---|
| Biomarker 1 | Sleep Duration Changes - Length Of Time In Bed Versus Sleeping Exceeds Limit. Need To Differentiate Between Sleep And In Bed For This. Need To Baseline Across Multiple Days To Determine Adverse Behaviors And Changes. | Reduced Activity - Activity Mapping Throughout The Day, Common Behaviors And Trends In Steps, Need To Differentiate Between Stress And Exercise As Part Of This. Determining Outliers May Require Exercise Recipes And Stress Management. Steps Inside A Room May Spike A Degree Of Stress When Within A Circular Fashion, Duration Of Time And Speed; Versus Exercise In A Mostly Straight Path With Increased Linear Acceleration, Versus Reduction Of Activity When Individual Is Mostly Sitting Or Sedentary. A Prior Predictor May Reduce False Positive In Some Scenarios Such As A Stressful Indicator Or Asleep Duration Change. | Communicative Expression Changes - Changes In Tonality Of Voice, Or Facial Expressions Could Indicate Changes In Pain. Classifying Baseline Measurements And Scenarios Such As Sickness And Healthy Behaviors Can Help To Identify Changes In How The Body Presents Itself To Others. |
| Biomarker 2 | Social Proximity Indicator - Avoidance Or Acceptance And Duration Of Time Around Others, Periodicity And Specifycity To Multiple Days And Weeks To Determine Profiling Of Personalization To Detect Changes Is Needed. | Cognitive Alertness - Reduced Responsiveness Or Ability To Control Aspects, Motor Skills Has Reduced To A Detectable Threshold. This May Also Be Indicative Of Substance Abuse And May Require Depression Recipe To Provide Additional Precision. | Gait Changes - Detecting Changes In Limping Or Distance Between Strides On The Left Or Right Side Can Help Determine If The Individual Is Crouching Or Has Migraines Or Other Pain Areas, Which Is Overtasking The Person And Redirecting Their Cognitive Ability To Walk As They Normally Would. |
| Biomarker 3 | Substance Abuse Indicator - Changes In Cognitive Outputs Combined With Detected Differences Between Fatigue Versus Substance Abuse. May Require Fatigue Recipe To Provide Additional Precision. | Sleep Quality - Sleep Disrupters Within A Contiguous Line Of Sleep May Be Indicative Of Fatigue Increments Throughout The Day, And Provide Performance Improvements When This Improves From An Engagement Mechanism. | Physical Adjustment Frequency - The Inability To Sit Still Or Sleep In A Still Manner, With Constant Movement, Or Turning/tossing About While Trying To Find Least Painful Position Is Indicative Of Increased Pain Levels Related To The Increased Frequency Of Movement. |

FIG. 5B

| | | | |
|---|---|---|---|
| Value Triggers | Over 11 Hours Of Time In Bed, No Public/Social Involvement, Decreased Cognition And Gait Changes Suggesting Depressive Or Abusive Behaviors. | Less Than The Number Of Steps Required To Walk To The Bathroom Every 2 Hours, Decrease Cognition And Gait Changes Suggesting Alertness Reduced, Time Asleep Throughout Time In Bed Totals More Than 6 Hours. | Irregular Expressions Suggesting Behavior Change, Decrease Cognition And Gait Changes Suggesting Behavior Change Indicative Of Pain, Physical Adjustment Frequency Increasing. |
| Outcome Goals | Computer Detected Depressive Episodes For Engagement Messages To Increase Overall Engagement And Reduce Reoccurrence Of Depressive Episodes Due To Manage Sleep, Social And Substances-Reinforced By Medication, Bioinformatics And Omics. | Computer Detected Fatigue Related Impairments For Engagement Messages To Reduce Fatigue Due To Regular Activity, Heightened Cognition And Sleep Quality Factors-reinforced By Medication, Bioinformatics And Omics | Computer Detected Pain Related Impairments For Engagement Messages To Capture Pain Self-Reported Values And Correlate Changes In Expression /Gait With Adherence To Medication And Pharmacogenomics. |
| Failure Points-Example | Engagement Messages To Promote Healthy Options And Things To Suggest Personality Improvements Like Exercise, Talking With Others, Lessening Substance Abuse To Demonstrate Previous Return Of Value To Participant Where They Had Successes Earlier And How They Were Able To Overcome | Engagement Messages To Promote Rest And Relaxation, Pharma And Stress Reduction Technique And Considerations For Previous Success Measures | Engagement Messages To Collect Self-reported Pain Measurements And Trend Them Over Time To Suggest What Protectors And What Triggers Are Present To Identify How To Better Manage These, Possibly Include Fatigue Recipe Or Depression If Individual Requires Additional Support To Better Manage. |
| Success Points-Example | Unlock Reward Goals To Demonstrate Milestones Achieved And How To Safety Congratulate Yourself With Doing Something Fun Without Slipping Back Into A Depressive Episode. | Unlock Additional Complexities Of The Program For The Individual To Continue To Drive Deeper Cognitive Control And Value Points With The Program. | Proper Pain Regulation Over A Long Time Can Demonstrate Skills Educated Throughout This Process And As Such Additional Recipes Could Be Turned Off Or Accessed For Allowing Other Areas Of Mind And Body Balance Opportunities. |

FIG. 5C

ADAPTED DIGITAL THERAPEUTIC PLANS BASED ON BIOMARKERS

FIELD OF THE INVENTION

The present invention relates to the field of digital therapeutics and the adjustment of software applications and software modules using biomarkers and biosignature files, and more specifically an adjustable biostream self-selecting system (ABSS). Through a plethora of inputs, the system associates therapeutic recipes and associated biomarkers in a personalized approach to recommending an individual to a specific therapeutic program. Therapeutic programs operate in accordance with personalized inputs suggested by the user, and through digital markers and biomarkers, trigger new recommendations by "knowing" the individual. Each bio-stream contains information utilized within these biomarkers to trigger additional therapy recommendations such as behavioral or medicinal pharmacogenomics, advisory suggestions through phenotyping, and supplemental omics, such as epigenomics through epigenetic factors, which could result in findings such as cancer. Because of the complexity of the plurality of inputs, these biomarkers are managed in a way that enables low-latency detections, low bandwidth needs, low processing needs, and less battery needs. The pre-processing of these biomarkers helps additional therapy management and precision medicine across larger global population needs of the system.

BACKGROUND OF THE INVENTION

Current health related technological environments and services include user device applications and other platforms which collect bioinformatic data. These known systems use the bioinformatic data to create therapeutic plans to treat certain types of diseases and ailments, for example.

These current collection applications/software collect all information related to the user. However, current bioinformatic data systems are inefficient in several areas. First, current systems collect and process unnecessary data which is not relevant to the therapeutic plan. The collection and processing of unnecessary data is both inefficient from a processing standpoint and clogs networks with unnecessary data and communications. The unnecessary processing and data also consume power and the processing time of many devices. These inefficiencies cost both the provider and user.

In addition, known systems have no, or very limited, ability to learn specifics about the user or recipient, and how to apply known aspects to create tailored therapeutic plans or tailored therapeutic applications. Ideally, a system could tailor an application and therapeutic plans ideally configured and suited to treat each person with their unique health needs.

Therefore, technical improvements and solutions are needed to overcome these technical problems while accommodating the evolving needs of users. The systems and methods of the present invention provide such improvements.

SUMMARY OF INVENTION

The present invention provides a network, system, or device for dynamically adapting and displaying at least one personalized therapeutic plan, comprising: a processor including instructions on a non-transitory computer medium, the non-transitory computer medium constituted by one or more data storage mediums; the instructions, when executed by the processor, configures the recipient device to: activate at least one controller for controlling the precision of at least one data signal; activate a biostream comparator for combining data from the at least one controller; a therapeutic plan resident on device and associated with a user of the device; a plurality of biomarker configuration profiles resident on the device; activate a biomarker configuration profile manager, the biomarker configuration profile manager using the therapeutic plan to select one of the plurality of biomarker configuration profiles; initialize the device to observe a plurality of bioinformatic data from a plurality of data sources and using the selected biomarker configuration profile and the at least one controller to generate at least one configured biostream; process the at least one configured biostream through the comparator to generate at least one biomarker; and updating, by a therapeutic plan manager, the therapeutic plan based on the at least one biomarker.

The network, system or device can then update the therapeutic plan by a therapeutic plan manager selecting a new therapeutic plan, or by modifying the existing therapeutic plan. The device (i.e. client device) can be in bi-directional communication with the plurality of data sources, and the plurality of data sources can include one or more sensors. Further, the plurality of data sources may be comprised of one or more directly observed data sources, passively observed data sources, indirectly observed data sources, publicly observed data sources, or comparatively observed data sources.

The present invention may use the biomarker configuration profile or profiles to interact with the controller to control the data sources or sensors. The controller can control the data streams or sensors by activating or deactivating the data streams or sensors. The controller can refine or control the data streams or sensors in a myriad of ways, including smoothing the biostream signal, generating a signal derivative, or detecting signal peaks. The therapeutic plan resident on the device can be selected by the user during initialization or selected or installed by the system or processor during initialization. The biomarker or biomarkers generated by the system can be used to configure the software application configuration profile of the application resident on the device. The application having at least one therapeutic application module. Further, the biomarker or biomarkers can be used to instruct a therapeutic module manager to configure the application with at least one therapeutic application module which might include initiating an update of the application to include the at least one therapeutic application module.

The present invention also provides a system of networked devices that provide adaptive therapeutic plans, with the processing being performed over a network, to provide communication interface amongst the networked devices. Each of the devices in the network is in the form of a tangibly embodied computer processor, with each computer processor including instructions on a non-transitory computer memory. The system comprises the network, over which a plurality of networked devices communicate, and a biostream processor device including biostream instructions. When the biostream instructions are executed by the biostream processor device, they configure the biostream processor device to: activate at least one controller for controlling the precision of a data signal (which may be one of the bioinformatic data sources); activate a biostream comparator for combining data from the at least one controller; activate a biomarker configuration profile manager, the biomarker configuration profile manager selecting a therapeutic plan, from a plurality of therapeutic plans, to select a biomarker configuration profile from a plurality of biomarker configuration profiles; initialize the plurality of connected devices to observe a plurality of bioinformatic data from a plurality of data sources and using the selected biomarker configuration profile and the at least one controller to generate at least one configured biostream; and process the at least one configured biostream through the comparator to generate at least one biomarker;

A client device can include client instructions that, when executed by the client device, configure the client device to: communicate with the biomarker processor device to receive the at least one biomarker, the at least one configured biostream, and the selected therapeutic plan; select one or more therapeutic modules available to the client device, based on the selected therapeutic plan and the at least one biomarker, to configure a therapeutic application resident on the client device; and adapt the selected therapeutic plan on the client device by adapting the one or more therapeutic module in the configured therapeutic application based on observed data from the configured biostream.

The present invention also provides a device for dynamically adapting and displaying at least one personalized therapeutic plan. The device has a processor including instructions on a non-transitory computer medium, the non-transitory computer medium constituted by one or more data storage mediums. The instructions, when executed by the processor configures the recipient device to: conduct a scan to identify at least one health data biostream available and related to a recipient associated with the device; receive a communication having at least one biosignature data file, and a plurality of biomarker attributes, the biomarker attributes having a plurality of therapeutic profile configuration attributes: analyze the at least one biosignature data file, the plurality of biomarker attributes, and the plurality of therapeutic profile configuration attributes to generate a personalized therapeutic profile for the recipient; determine a final therapeutic application configuration using the personalized therapeutic profile, for a therapeutic application resident on the device and consisting of at least one therapeutic related module contained within the therapeutic application; generate at least one therapeutic plan available through the therapeutic application based on the personalized therapeutic profile and the final therapeutic application configuration; generate at least one biostream configuration profile based on the at least one health data biostream and the at least one therapeutic plan; select, by a therapeutic plan manager, one of the at least one therapeutic plan; select, by a biostream configuration profile manager, one of the at least one biostream configuration profiles based on die selected at least one therapeutic plan; and control the filtering of data of the at least one health data biostream.

The present invention also provides a method for dynamically adapting and displaying at least one personalized therapeutic plan on a recipient device within a network of networked devices. The method comprises: activating, by a biostream processor device, at least one controller for controlling the precision of at least one data signal (which may the one of the bioinformatic data sources); activating, by the biostream processor device, a biostream comparator for combining data from the at least one controller; selecting, by the biostream processor device, an initial therapeutic plan, from a plurality of therapeutic plans; selecting, by the biostream processor device, a biomarker configuration profile from a plurality of biomarker configuration profiles; initializing, by the biostream processor device, the plurality of connected devices to observe a plurality of bioinformatic data from a plurality of data sources and using the selected biomarker configuration profile and the at least one controller to generate at least one configured biostream; process the at least one configured biostream through the comparator to generate at least one biomarker; transmitting, by the biostream processor device to a client device, the at least one configured biostream and the selected therapeutic plan; selecting, by the client device, one or more therapeutic modules available to the client device from the network, based on the selected therapeutic plan and the at least one biomarker, to configure a therapeutic application resident on the client device; and adapting, by the client device, the selected therapeutic plan on the client device by adapting the one or more therapeutic module in the configured therapeutic application based on observed data from the configured biostream.

BRIEF DESCRIPTION OF THE DRAWINGS

The present invention can be more fully understood by reading the following detailed description together with the accompanying drawings, in which like reference indicators are used to designate like elements, and in which:

FIG. 4 depicts a diagram of the therapeutics layer of the present invention;

FIG. 5A depicts part one of an exemplary therapy recipe plan or plans for treating cancer;

FIG. 5B depicts part two of an exemplary therapy recipe plan or plans for treating cancer;

FIG. 5C depicts part three of an exemplary therapy recipe plan or plans for treating cancer;

DETAILED DESCRIPTION OF EXEMPLARY EMBODIMENTS

Hereinafter, aspects of the methods and associated systems in accordance with various embodiments of the invention will be described. As used herein, any term in the singular may be interpreted to be in the plural, and alternatively, any term in the plural may be interpreted to be in the singular. It is appreciated that features of one embodiment as described herein may be used in conjunction with other embodiments. The present invention can be more fully understood by reading the following detailed description together with the accompanying drawings, in which like reference indicators are used to designate like elements.

Figure 1:
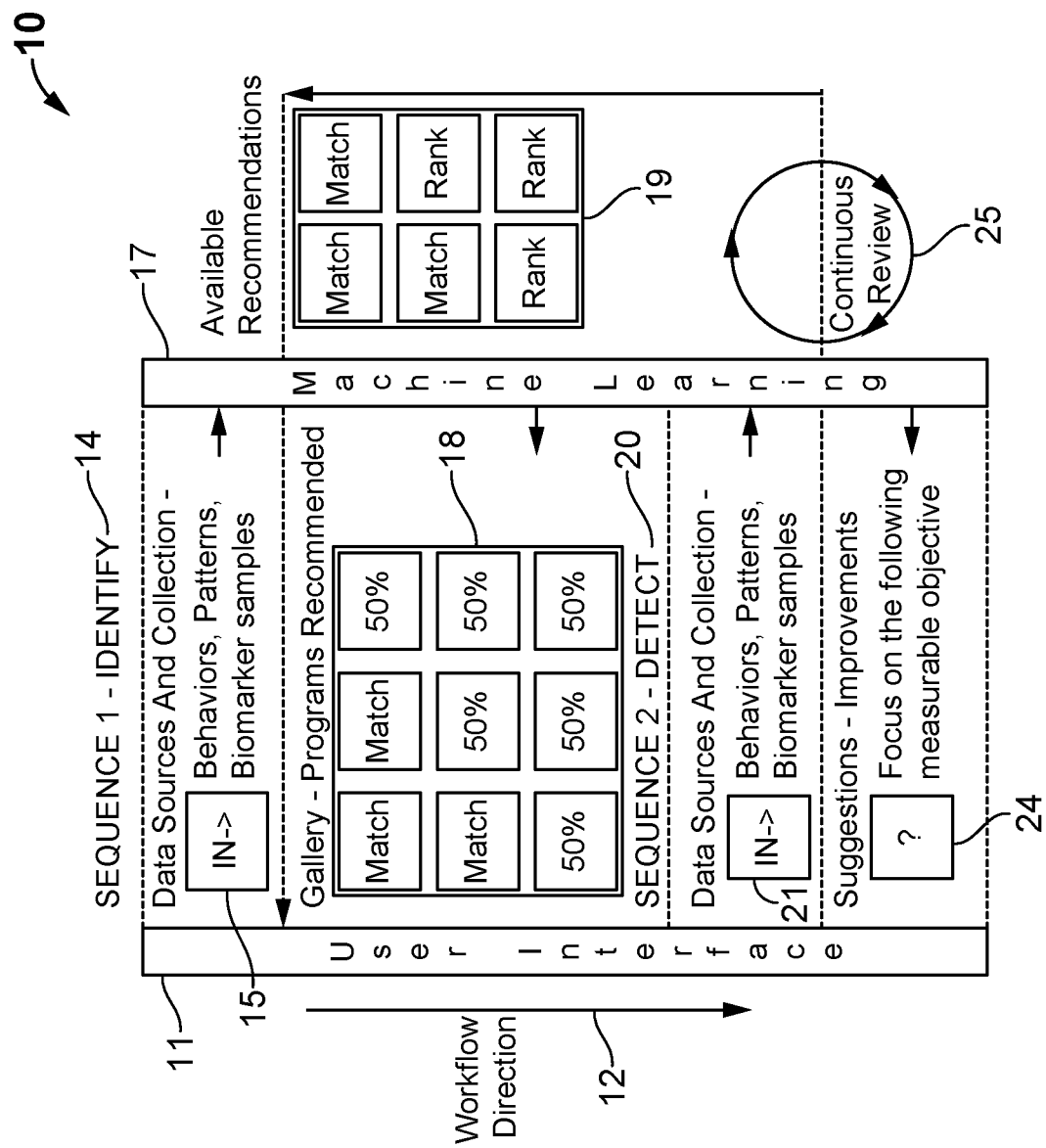
FIG. 1 depicts a workflow of the application gallery customization feedback.

FIG. 1 shows two sequences of the workflow of the system 10 through the inputs of the user interface 11 and the recommendations, observations, and interventions of the computer processing and machine learning 17 management of user inputs. "Sequence 1—Identify" 14 shows an initial procedure where the individual's needs are identified and therapy recommendations are proposed as a gallery of recommended programs 18. The user's individual needs are determined based on the information obtained after the user downloads or remotely accesses the user interface 11. The system begins learning the individual by collecting a series of sensor data inputs from directly connectable wearables, passively sensed remote client data, indirectly sensed inputs from remote client data, publicly available sources, and comparative sources from other individual data sources to collect, observe and survey data inputs 15 related to the individual. The observed inputs 15 include data collection of behaviors, behavior patterns, biomarker samples, and surveys as the workflow starts and the application is installed, or remotely accessed, and registration begins. All of the data collections, observations and survey data inputs 15 information come together to personalize and identify who the user is and to give a gallery of therapeutic program recommendations 18 available on the client or from the back-end server side. Initially, the gallery of therapeutic programs recommended 18 are discovered from all available recommendations 19 and the chosen programs are based on personalization, filtering technique or unfiltered depending on the permissions of the individual user. The data collections, observations and survey data inputs 15 are run through the computer processing and machine learning 17 process to determine the most accurate therapeutics program, configured therapeutics plan or specified module and its attributes applicable from all of the available therapeutics programs 19 to the user and other users of the system as determined by permissions. Once the appropriate therapeutics have been defined, the user is presented a gallery of recommended therapeutic programs 18, describing observations and interventions that are highly probable to be the most applicable to user, and recommends a gallery 18 for the user based on the individual user's up-to-date processed data collections and sampled information. The gallery 18 provides a mobile device user with specific therapeutic recommendations to follow/maintain/show results against.

Therapeutics are created by an administrator, or a user of the system as an administrator, by both customizing therapy and program builder recipes or creating new therapy and program builder recipes from scratch. Multiple therapy recipes that exist define very specific biomarkers and digital markers for collection and engagement with the individual. The program builder is a system component that allows the admin to create a personalized experience for engaging with a set of therapeutic recipes with consent, content and personalization. All of the therapeutic recipes or plans are fully customized to be displayed prominently in the individual's gallery while launching the application for the first time, with continued engagement and recommended programs for the individual to be part of. Therapeutics and related areas of health/wellness include, Bone/Osteoporosis, Immunology, Orthopaedics, Cardiovascular, Infectious diseases, Pulmonology, Central Nervous System (CNT), Inflammation, Psychiatry, Dermatology, Internal diseases, Respiratory, Diabetes, Metabolic diseases, Rheumatology, Endocrinology, Nephrology, Surgery, Ear Nose Throat (ENT), Neurology, Urology, Gastroenterology, Oncology, Vaccines, Hematology, Ophthalmology, Thrombosis.

The therapeutic plans and modules are delivered to the individual when they go to the web application or mobile application client, and the individual can login or register and select a particular therapeutic program from the gallery. Such a program could be specific to a group/organization, a disease, a genomic trait, or some ideal state that the individual would like to aspire to.

"Sequence 2—Detect" 20 shows a continued procedure where the individual's needs are continuously reviewed for digital markers and biomarkers. "Sequence 2—Detect" 20 continuously collects, observes and surveys data inputs 21 by measuring an individual's behaviors, their patterns through data sources and biomarker samples, which produces suggested improvements 24 through intervention recommendations and measurable objectives and can feed into "Sequence 1—Identify" 14 and repeats the workflow 12. The data collections, observations and survey data inputs 21 undergo continuous review 25 to ensure the most accurate and applicable therapeutic programs measurable objectives are being met by the individual. The continuous review 25 can cause the machine learning 17 to refine accuracy through data observations, compare biomarkers, behaviors and patterns to a selected therapeutic plan and make new therapeutic plan recommendations 19 for all users of the system. The machine learning 17 will intervene and make personalized suggestions and engagements for an individual's improvement 24 of the currently selected therapeutic programs that focus on following measurable objectives of each therapeutic plan within that program.

An individual's usage of a therapeutic can include continued usage of the program, wherein it collects biomarkers, bioinformatics data stream (referred to as a "biostream") samples either by computer-assistive reporting or self-reporting, and by managing the engagement messages to help drive outcomes through the interventions applied by the program. An individual's continued success can then be measured and return of value for positive reinforcement.

The different therapies monitored within the therapeutics described include but are not limited to surgery support, cancer survivorship, disease management such as diabetes, fitness habits such as physical therapy, mental wellness such as depression, eating habits such as dieting, addiction reprieve such as opiates, social support such as post-traumatic stress disorder (PTSD), and sleep habits such as insomnia or apnea. The therapeutic models and modules monitor biomarkers/markers such as cardiac related, respiratory related, neuro related, physical related, environmental related and additional interactions.

The system also builds personality models for the user in order to determine the correct therapeutics. The personality models include appearance relevancy, feature relevancy, and personalized profiles. The personalized profiles include personality type, gender identification, general user demographics, common locations, ownership details, measured environment and environment exposure, measured physiology such as vital, electronic health records (EHR) and omics, measured activities such as assessments, electronic patient reported outcomes (ePRO), and task, and measured economy. Omics involves studying scientific areas of medicine and biology such as the genome in genomics, or nutrition in nutrigenomics—study of the genome and the interaction with nutrition with regard to treatment and prevention, and pharma in pharmacogenomics—study of the genome in drug response; these among other omics allow for phenotyping traits and biomarkers for therapeutics at a precision level. The ability to develop and broaden biomarkers and bioinformatics defines linkages and relationships to many other studies, which include supporting: epigenomics—studying the variability of deoxyribonucleic acid (DNA) and modifications through phenotype plasticity and gene regulation, among more specific areas like the proteome in proteomics—study of proteins, and the metabolome in metabolomics—study of metabolites. Other omics could include, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metallproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics.

Personalization can be due to multiple reasons such as single nucleotide polymorphisms (SNPs) and the genetic variation and microbiome composition. The recommended gallery 18 allows a device to be a specifically tailored application with very specific tailored sub programs. The recommended gallery 18 is a process by which the system takes the application and looks at sub-programs in the gallery. The system then chooses the best subprogram in a selection and refinement process. Ultimately, the user ends up with a very specific tailored application with very specific tailored sub-programs that have the specific therapeutics that are most relevant to the user.

Figure 2:
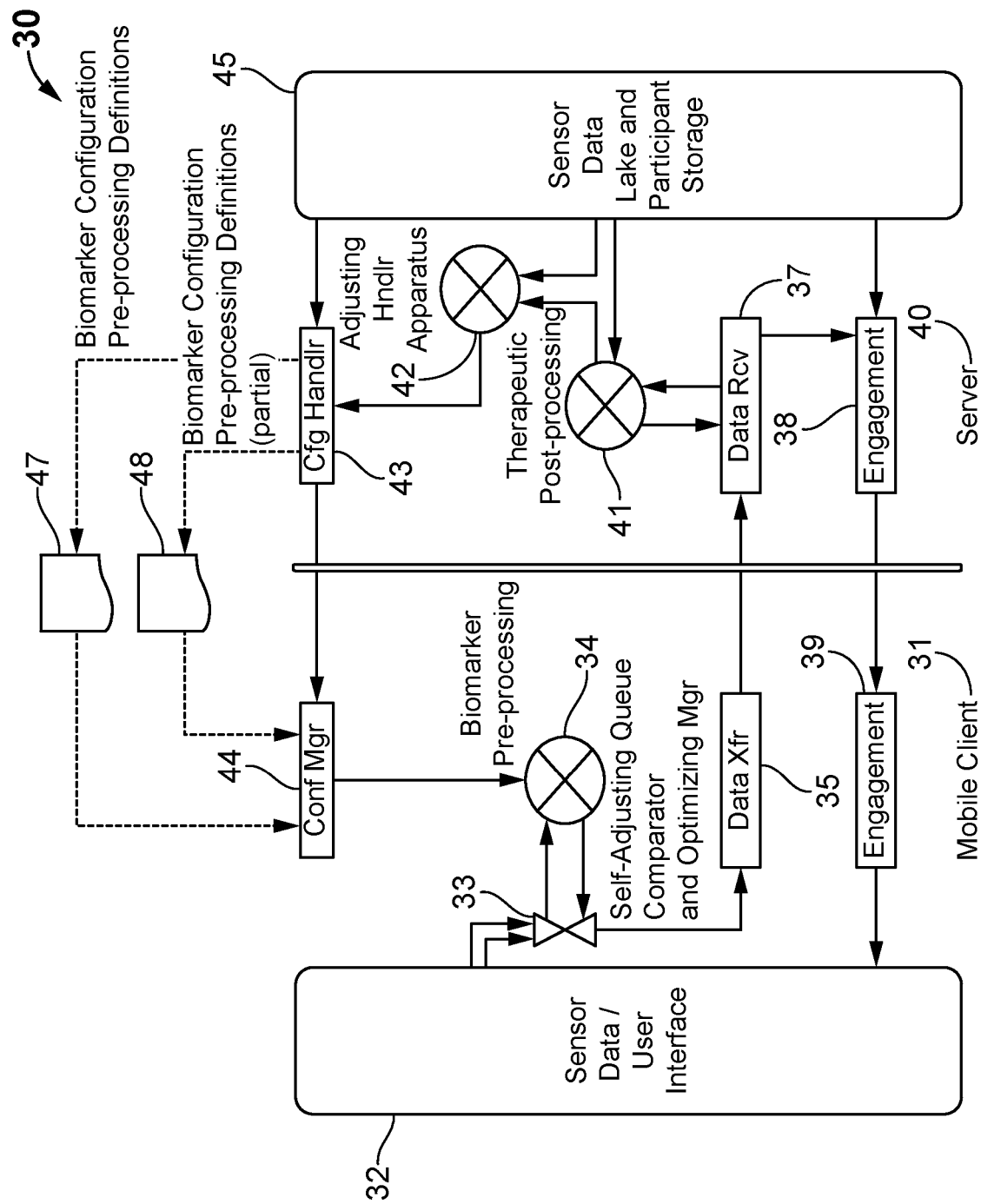
FIG. 2 depicts a general system overview diagram.

FIG. 2 describes the general system 30 with regards to the application on the mobile client 31 and software components of the server 40. The general system 30 decides what to and what not to process. The system 30 looks at what data processing should be skipped in order to improve processing/network/bandwidth needs. The general system 30 takes the sensor data/user interface 32 of the mobile client 31 and filters the data through the self-adjusting queue comparator and optimizing manager 33. The data from the self-adjusting queue comparator and optimizing manager 33 is sent to biomarker pre-processing 34 which logs it and sends it back to the self-adjusting queue comparator and optimizing manager 33. The self-adjusting queue comparator and optimizing manager 33 then sends the selected sensor data 32 to the data transfer (or Xfr) 35, which sends data to the data receiver 37 on the server 40. The data receiver 37 sends the selected sensor data to the therapeutic post processing 41, which logs it and sends it back to data receiver 37. Data receiver 37 then sends the selected data to engagement 38, which passes along the data to engagement 39 and subsequently returns it to sensor data/user interface 32. The therapeutic post processing 41 also received data from sensor data lake and participant storage 45. After processing the data, the therapeutic post processing 41 sends the data to the adjusting handler apparatus 42, which also received data from the sensor data lake and participant storage 45. The adjusting handler apparatus 42 sends the selected data to the configuration handler 43. The configuration handler 43 also obtains data from the sensor data lake and participant storage 45. The configuration handler 43 transfers the data to biomarker configuration pre-processing definitions 48 and 47, which transfer the data to the configuration manager 37. The biomarker configuration pre-processing definitions 47 is a full and complete definition of amount of data transfer over air, and biomarker preprocessing definition 48 is a partial definition for real time live changes that are slight modifications based on adjustments about limits to decrease false positives. The configuration manger transfers the selected data to biomarkers pre-processing 34.

One important aspect of the present invention is the system's ability to decide what data to process and how to minimize (or maximize the efficiency of) certain processing resources. The system has the ability to be selective in the collection of data, filtering of data, or refinement of data it collects and processes. A common issue with large pools of data is the inability to sort such large amounts of data and the inability to find accurate or useful data. The system of the present invention is able to decide which data to restrict, reduce, filter, or process to focus the collection of data to truly important data. Sometimes it is not the data that is important but the transition between one data element or type to the next. The system makes use of one or more types of configuration profiles of files. One important type of configuration profile, which is tied to the recipient and the therapeutic plan, is a data configuration profile which enables the system to match data needs to the components or sensors available. This bioinformatics data configuration enables the system to turn on/off, activate/deactivate, adjust signal parameters for signal averaging and latencies through Fourier transforms and signal-to-noise ratios for signal smoothing or vary the sampling frequencies and duty cycle of the signal sampling durations of device components, sensors, and other inputs or outputs as necessary. The system looks at what data comes into the devices, how data comes in, whether the data can be processed up front, and if the data can be compared or optimized through a manager, controller, or comparator. The system can process, compare and refine data to configure data in the form of one or more biomarkers associated with the recipient or user of a device. The data can be configured through one or more multi-set rules or processes which might also allow the data or files to be stored and used locally so the device can work in an offline mode. The system or device may need an offline mode capability because being online all the time costs: latency of signal processing across a network, bandwidth requirements for reducing latencies and managing storage needs, total system network processing, battery utilized in managing data transactions and network status and messaging needs, and money in terms of data usage and cost of operating; or a network may not be available resulting in delay of care as the therapeutic plan needs to be active in order to deliver a continually engaging system of record. The present invention also enables the system to make a smarter internet-of-things (IOT) framework specific to biomarkers and therapeutics.

Figure 3:
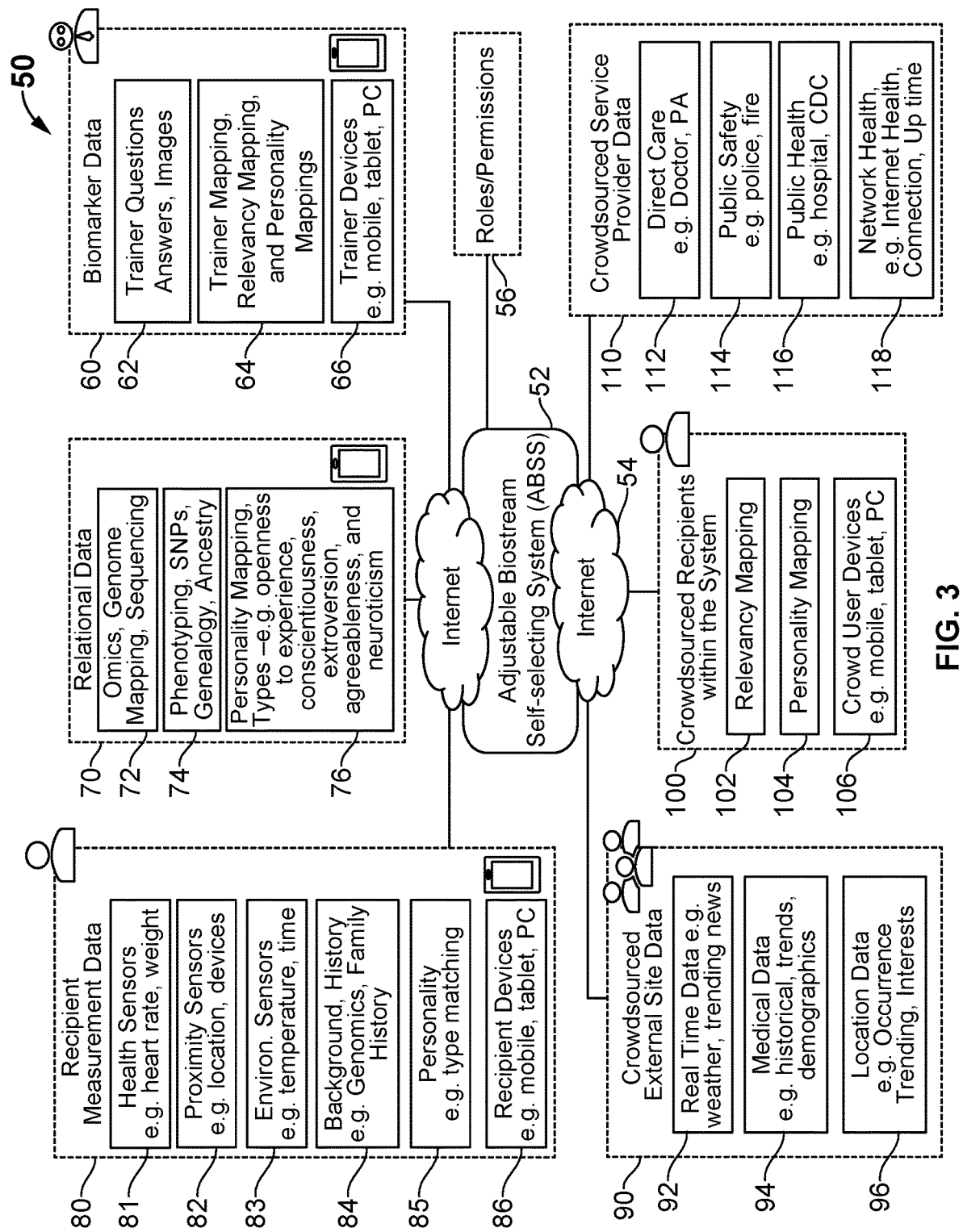
FIG. 3 depicts an overview diagram of the network and related systems.

As shown in FIG. 3, the system utilizes significant amounts of data to adapt the adjustable biostream self-selecting system, ABSS 52, e.g., adapting the application architecture using real time data. The network 50 of the present invention includes the adjustable biostream self-selecting system 52 which is connected via the Internet 54 or other communication methods to numerous devices and data. These devices and data segments include biomarker data 60, relational devices and data 70, recipient measurement devices data 80, crowdsourced external site data 90, crowdsourced recipient data within the system 100, and crowdsourced service provider devices and data 110. The adjustable biostream self-selecting system 52 is also accessible by one or more admins and users having roles and permissions 56, as set forth in the systems roles and permissions sub-system.

Within the biomarker data 60, therein includes trainer questions, answers, images 62, trainer mapping, relevancy mapping, and personality mappings 64, and trainer devices, e.g., a mobile device, a tablet device, or a PC 66.

The relational data 70 includes Omics, including: Genomics, Nutrigenomics, Pharmacogenomics, Genetics, Genome Mapping, Gene Sequencing, Epigenomics, Proteogenomics, Metabolomics 72, Genealogy (genes, carrier, traits, risks), Phenotyping, SNPs, and ancestry data 74, and personality mapping data 76. Personality mapping data 76 may include data on personality types, such as whether a recipient is open to experiences, consciousness, extroversion, agreeableness, neuroticism, and other known types.

The recipient measurement section 80 includes health sensors 81, proximity sensors 82, environmental sensors 83, background data 84, personality data (type matching) 85, and recipient devices 86. Health sensors 81 might include things like heart rate and weight monitoring of data and would provide physiological data measurements. The proximity sensors 82 might include things like location sensors and devices with location tracking data and would provide activity related data measurements. The environmental sensor 83 would include sensors measuring temperature, time, passively sensed, ancillary, or other directly reported data sources relevant to contextual cues and measured environment data. The background and recipient historical data 84 might include specific longitudinal history of the recipient, including genomics, and family history. The personality data 85 might include personality type matching information. Recipient devices 86 might include the types of devices such as mobile devices, tablet devices, PCs, the operating systems within those devices, and how they are used, and the device used as a sensor.

The external crowdsourced section 90 might include real time data 92, medical data 94 and location data 96. The real time data 92 might include data such as weather or trending news, and would provide economic related data measurements. The medical data 94 might include historical data, trending data in terms of population (upward and downward risks, emerging, outbreaks, epidemic, and pandemic) and demographic data. The location data 96 might include occurrence data, trending data, and interests.

In addition, as seen in FIG. 3, the system may include internal or system crowdsourced data 100 of recipients, relevancy mapping 102, personality mapping 104, and recipient devices 106.

Further, the crowdsourced service provider data 110 may include direct care 112, public safety 114, public health 116, and network health 118. The direct care 112 would include devices and data for the direct care, which provides information that is de-identified by a recipient's doctor or physician's assistant. Public safety 114 would include devices and data such as police and fire or water and power through varying channels like public broadcast information. Public health 116 would include devices and data such as local hospitals, ambulatory and CDC information. The network health 118 would include devices and data based on internet connections, internet or provider health, uptime, and other similar network and communication-based information.

The network 50 includes interaction amongst application section 60, relational section 70, recipient measurement section 80, external crowdsourced section 90, internal crowdsourced recipient section 100, and crowdsourced service provider section 110 as used by the User Responsive Dynamic Architecture 53 to help formulate the ideal display for different users based on relevancy mapping 102, personality mapping 104 and other recipient-based elements to provide display of content relevant and related to the specific recipient.

FIG. 4 depicts a layered view of the system sensors, and processing elements 125 and their use cases as they generally apply to varying therapies, biomarkers, biomarker predictors, sensor classifiers, underlying sensors and equipment hardware and software related drivers. The use cases can be separated into 4 layers, sensors and drivers 127, sensor classifiers 129, biomarker predictors pre-processing tags 131, and therapeutic engagement post-processing determination 133. The sensors/drivers 127 layer is composed of a hardware or software component acting as a data source that can be controlled either through hardware or software to enable bioinformatics data source sensors, which the system can interact with, and associated drivers for controller related aspects of the system. Each sensor or pseudo-sensor may be a data source or input into the system with data available to be read and processed by the system or device. Each sensor or input can provide a stream or biostream of bioinformatic data that creates a flow of raw data with changing states, values and transitional elements. The system can interact with the sensors and the controls of the sensors including varying the scan frequencies and step level controls that cause variations in accuracy over a given depth, scale and time domain. These translate into high amounts of data storage, transfer rates, processor utilization from end to end when dealing with the highest sampling capable of the system. In some cases, this creates unnecessary burden on the amount of structured data that is analyzed, with higher end signal processing algorithms. It then requires a higher performance degree of managing multiple parallel sources to resolve latency, through time dependent mathematical functions of multiple processing units coordinating the signal. This problem is further promoted when attempted to produce real-time engagement messages, versus post-reporting processes, where time dependent mathematical functions are less of a concerning risk.

Categories of sensors can be grouped to simplify controls and triggers when enabling a set of sensors. These sensor classifiers 129 help define rule definition guides for these sensors and can create a layer of abstraction when hardware may have variations in its implementation across platforms or components. Sensor classifiers 129 give the system the ability to model data with meaningful classifiers, and allow the system to turn on and off sensors as needed based on classification. The sensor types include, but are not limited to: audio, networking, phone, environment, positioning & activity, and user storage and instructions.

The biomarkers pre-processing tags (predictors) 131 encompasses digital markers and biomarkers predictors that define situations and sensors of sensor systems are predictive of events. The present invention includes instructions for the system to identify candidate biomarkers and combine them into biosignatures predictive of the susceptibility or resilience to the development of chronic pain or diseases.

The events that the biomarker preprocessing tags 131 predict may include, utilizing audio sensors, location and some physiological detection to determine that an individual is sleeping or watching television. Sound detection is a common method for analyzing frequencies present and associating them to specific elements through classifying elements like the sound a bird makes, versus a train versus higher ultrasonic sounds from a television or an electric toothbrush. Sounds, like odors or scents, are very unique. Other patterns can include specific duty cycle behaviors that are recognized when utilizing the phone in a specific way, or how the phone is detected through its movements from the individual utilizing the equipment. These feature classifications help identify or ID key information about users.

When these suggestive tags are recognized they can be sent for further analysis of a therapeutic. These predictive markers or biomarker's raw predictive data can either be discarded or forwarded during specific conditions (e.g., every 24 hours when the individual is connected to Wi-Fi versus a cellular network and when other optimal conditions occur, such as bitrate should be more than a specified number of bits per second and should consume no more than a specified percentage of total bandwidth utilized by the phone). Raw data can also be compressed for offline storage while preparing for a later upload. The raw data is helpful in defining which outliers may be causing false positives, and as a system, the therapeutic biomarker configuration and associated biosignatures can be updated across all users of the system if sufficient trends are discovered. Further reducing false positives is necessary to continue to reduce bandwidth, processing and storage needs. Additionally, if a given biomarker is subsequently driving an engagement to an individual, accuracy improvements may further create a positive experience as the individual continues to adopt and engage with the application.

The application can be configured to be biomarker-driven for health informatics and therapeutics. The application can also be configured for a specific use case including, for example, how to apply IoT to therapeutics and other health domains.

Once digital biomarkers predictors are prepared and transmitted, these are utilized within therapeutic engagement post-processing determination 133 as behavioral use cases that are defined as a personalized recipe for the individual. These therapies can be across various areas such as physical wellbeing, mental wellness, food disorders, substance abuses, social avoidances, and sleep complications. The predictors are then validated through recipes and combined through personalized behaviors and relational data to form biosignatures that can be crowdsourced across comparative phenotypes related to varying omics.

If outcomes are not achieved, then suggestions can be made to further search for the best method in working with the individual and their participation. The individual is part of the overall system as a feedback loop. The system is attempting to determine how best to personalize to the individual, collect data from the individual, detect markers and biomarkers of the individual and then determine how they correlate to a given therapy.

If there are predictors of success or failure, the system must react by bolstering the behavior or by interchanging alternate routines or therapy modules that may provide improved success rates based on biosignature trends and biomarkers across other engaging crowd-sourced information data sources.

FIG. 5A-C provides (3) therapy recipes 140 for cancer survivorship 143, 145, 147, the personalization elements 151 asked or observed through collected data sources before the recommendation of a personalized plan 153, the biomarkers 155 required to continuously detect positive and negative changes, the triggers 157 utilized with these biomarkers 155, expected outcomes 159, failure point and success points examples 161 for engagement and recommendations. As a cancer survivor program personalized for a user, the individual could be subject to 1 or all 3 therapy plans 143, 145, 147, and more as they become available. Programs can be 1:1 to a recipe, or could include multiple recipes and turn on or off recipe as the individual progresses through the program.

Cancer survivors struggle with prolonged engagement utilizing mobile applications and interventions applicable. The system allows the ability to adapt to the needs of an individual as insights and predictors of specific use cases in order to drive better engagement and thereby interventions. Some of the use cases for cancer survivors that will help drive these outcomes include: risk of depression, alertness or fatigue, social avoidances, and pain tolerances. In predicting psychiatric problems, data observation leads to developing behavioral profiles and digital phenotypes as biomarkers. These degrees of digital markers are collected through various observations and feedback, such as: sleep observation, cognitive observation, social observation, and self-reported feedback.

Depression is a common mood disorder that can be inclusive of multiple factors as biomarkers and digital markers. This includes changes in sleep patterns such as sleeping too late or as sleep duration exceeds a specified limit. There may be a diminished ability to concentrate, lack of energy and lack of enjoyment in typical activities. Such diminishing activities include further social avoidance or staying inside too much and not communicating with the outside world.

Alertness is a state of attentive behavior and a measure of fatigue that can be inclusive of situations arising like lack of sleep or insomnia/disrupted sleeping, avoiding stimulants like alcohol, opioids, and tobacco; and being balanced with exercise and nutrition. Changes in mobile phone usage can be a predictor of alertness levels changing.

Avoidances is a coping mechanism characterized as being inclusive of social, ability to leave the home or domicile, and lack of overall communication as a means to reduce stressors. Decreased mobility here is considered a marker for avoidances.

Pain tolerance is an experienced characteristic that can be impacted by decreased cognition, reduction in sleep duration, increased fatigue, and reduced social interactions or social isolation. This can be self-reported by individuals using a Likert scale to measure the degree of pain that they are feeling as a measure of their current tolerance. Additionally, utilizing social markers can be predictors for changes in pain tolerances.

Of these observation areas, there is a direct correlation between measurements of sleep, cognition and social communication. Some of the biomarkers and digital markers include: sleep duration, cognition testing, and location classification, along with many contextual markers from bioinformatic data sources like noise, light, temp, radio frequencies (RF), phone activity and other variants.

Sleep duration is an important metric; it is the time that the individual is asleep, not just in bed. There are many sleep attributes that are subjective such as sleep stage and sleep quality. However, sleep duration is very much objective; both in a sleep lab and through varying sensors and passively sensed information that can be utilized. In general, a person is said to be sleeping well with more than 6 to 7 hours of sleep in a given day depending on age; this is outside of napping or awakenings and only speaks to total time asleep in a given day. Sleep duration as a measure is needed to increase alertness and other cognitive behaviors required for social interactions and healthy living. Established research concludes that the timing, duration and structure of an individual's sleep can be illustrative of circadian phase. One such sensor measure of sleep is sleep actigraphy. Sleep actigraphy can help detect sleep cycles and sleep duration. A marker for sleep deficits and sleep surplus durations would be collected for additional correlated cognitive and homestay limits.

Cognition testing involves using games like balloon reactionary time in popping the balloons and how that can change from day to day and hour to hour. PTSD and cancer survivorship are interlinked in the way an individual reacts throughout the day to varying stimuli. A test in the morning followed by a test in the evening may be sufficient. One such sensor measure of cognition is measuring risk, which can be measured using BART (Balloon Analogue Risk Task) and can subsequently measure reaction time and response to risk.

Location classification can be defined as a de-identified method to your current location either using global positioning systems (GPS), received signal strength indicators (RSSI) proximity tracking from Wi-Fi, Cellular or Bluetooth among other tracking sensor systems and show information about where you are rather than the exact location. For instance, knowing you are at the pub or a church are important cues that could describe a social relevance but also an addictive risk potential based on the location. Likewise, a library or your home might show an anti-social perspective that given enough duration day to day could stimulate engagement techniques to drive individuals to more conversational areas of interest. Tracking reported models like time spent against specific locations assist predictive biomarkers for possible risks such as a homestay risk.

Contextual markers help with the overall awareness of how to interpret information like physiological data. For instance, if sleep is disrupted, was it disrupted by noises like trains or snoring, or light because of an alarm or an airplane, or temp due to a dysfunctional heating, ventilation and air conditioning unit (HVAC). This can be helpful when reviewing varying disparate sources for a given therapy or biomarker that can dictate engagement levels. Sensors capable of measuring audible decibel levels, interpreting measured audio data, measuring luminance lux, interpreting measured light wavelengths, measuring temperature and gases or particles in the environment surrounding an individual.

Radio Frequency (RF) sampling can help with positional or proximity guidance inside of a home when considering Wi-Fi Bluetooth and cellular examples. This can give a relative guidance to social interactions like being in a public area when GPS isn't shared, and the increase Wi-Fi hotspots or nearby mobile phones and wearables increase or decrease in availability.

Phone activity can help in determining if the user is constantly using the phone, an app, or nearby other phones. For instance, on Android, and with mobile carrier specific application programming interfaces (APIs) we can determine the phone usage based on the call classification to a specific location like a pizza delivery restaurant. If an individual is always inside but not traveling to any location, and they are commonly calling delivery phone numbers, it might be a case of avoidance or depression depending on their case. Just knowing, for instance on a reduced permitted subset of phone usage details, such as iOS, that the individual is in a phone call can also be helpful as it can point to reaching out or a social need to connect in some environments or it can point to a reoccurring pattern of usage in behavior when considered overall or with other situations like riskier tendencies occurring when the user is at the pub and making frequent calls suggest intoxication. Overall, the ability to measure changes in phone usage behaviors will help with comparative analysis to other markers, for example, increased usage when there is a decrease in pain versus pain tolerance.

These biomarkers and digital markers assist the system in continued insights to suggest interventions and re-engagement messages that continue to complement the usage of the application and system while collecting additional bioinformatics. The system allows for an intervention to continue data observations in parallel with this.

Figure 6A:
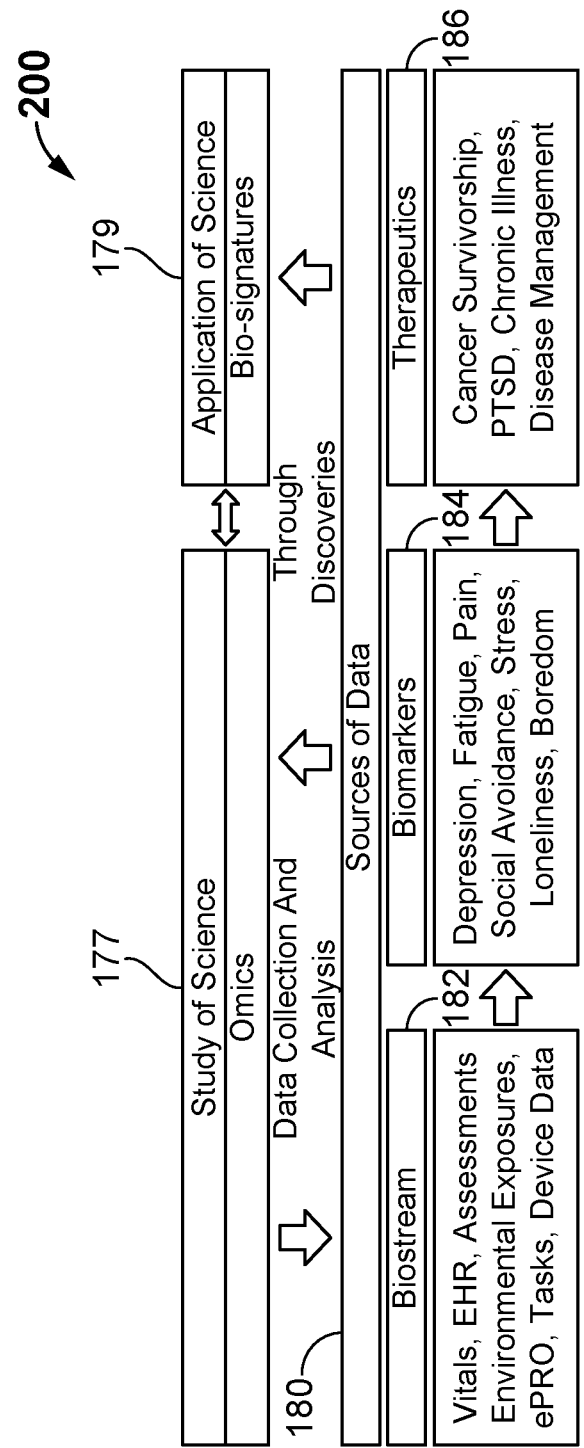
FIG. 6A depicts a general flow diagram of the use of omics, data and biosignatures leading to therapeutic discoveries.

FIG. 6A describes the science of data and discoveries. Omics 177, the study of scientific areas of medicine and biology, is in a feedback loop with the sources of data 180 and the application of science, i.e. bio-signatures 179. The system has omics 177 perform data collection and analysis from different sources of data 180, such as biostream 182, biomarkers 184 and therapeutics 186. The biostream 182 data includes vitals, EHR, assessments, environmental exposures, ePRO, tasks, and device data. Biomarkers 184 data includes depression, fatigue, pain, social avoidance, stress, loneliness, and boredom. The therapeutics 186 data include information on cancer survivorship, PTSD, chronic illness, and disease management. The biostream 182 data feeds into biomarkers 184, and biomarkers 184 feed into therapeutics 186. These sources of data 180 are collected by omics 177 and biosignatures 179. The omics 177 and biosignatures 179 share the data through discoveries. The analyzed data is fed back into the sources of data 180 for a refinement of the biostreams 182, biomarkers 184 and therapeutics 186.

Biostream

A bioinformatics data stream, or Biostream 182, traditionally refers to a real-time biomedical and health care data stream. These biostreams 182 provide a compendium of data aggregated using health-monitoring devices or data generated and captured in EMR and other health care software systems during ambulatory care, inpatient visits, or any health data monitoring period, which may aid in diagnosis, prognosis, interventions and stratifications. A biostream is the plurality of signal inputs aggregated through the client as a time domain controller where biostreams have varying degrees of sampling methods, enablement practices and are utilized to generate biomarkers for use in observation and intervention of a given therapeutic plan. The present system uses a vast array of sensors to capture biostream 182 data on a continuous basis, not just during ambulatory or inpatient visits. These sensors may include heart rate monitoring, scales, GPS sensors, etc.

The user or recipient's device may be used to capture the biostream data, or the system's network of devices can be used to capture or receive data. Such data can be directly observed, passively observed, indirectly observed, publicly observed, or comparatively observed. Directly observed data is typically obtained through reported data sources by means of a device privately connectable to a data source such as, for example, a wearable patch measuring EKG or EEG, or a handheld remote blood analysis sensor for analyzing ketone levels for cancer patients, diabetics and others. Passively observed data is typically obtained through reported data sources by means of a personally inferred privately collectable data source such as, for example, a mobile phone, or a local application reporting EHR data.

Indirectly observed data is typically obtained through reported data sources by means of a remotely reported private data source, such as, a sleep reporting web service connector of an in-bed sleep sensor, or genomic reported lab data. Publicly observed data is typically obtained through reported data sources by means of an openly available data source, such as an environmental reporting service of local and globally available sensor data, or common phenotyping attributes. Comparatively observed data is typically obtained through an in-system multi-individual data source, such as local data lake.

The system can manage the precision of biostreams by implementing a comparator and a controller for a given biomarker configuration. Through the use of selected therapeutic 186 plans a biomarker profile manager selects one of a plurality of biomarker configuration profiles on the user device. The selected biomarker configuration profile interacts with the biostream data comparator processor and a biostream controller to generate the plurality of biostreams that will generate the biomarker. A biostream controller or controller unit controls signal input precision for biostreams by configuring, smoothing, creating signal acquisition derivatives, and peak detection. A comparator or comparator unit filters data from the controller with configuration while specifying signal enablement for bioinformatics data streams based on required needs of the biomarker. A biomarker processor unit receives the derived data from the comparator and controller for the identified therapeutic plan.

Through use of the biostream controller and a biostream comparator, the client side or device system is able to adapt to the following needs of the therapeutic plan and biomarker. Another benefit of the present invention is the trade-off in signal response time versus signal interpolation error which can be mitigated by increasing the responsiveness, by adjusting for a lower sampling rate, or by decreasing smoothing while detecting signal derivatives to adjust the dynamic responsiveness of disparate signals.

Figure 6B:
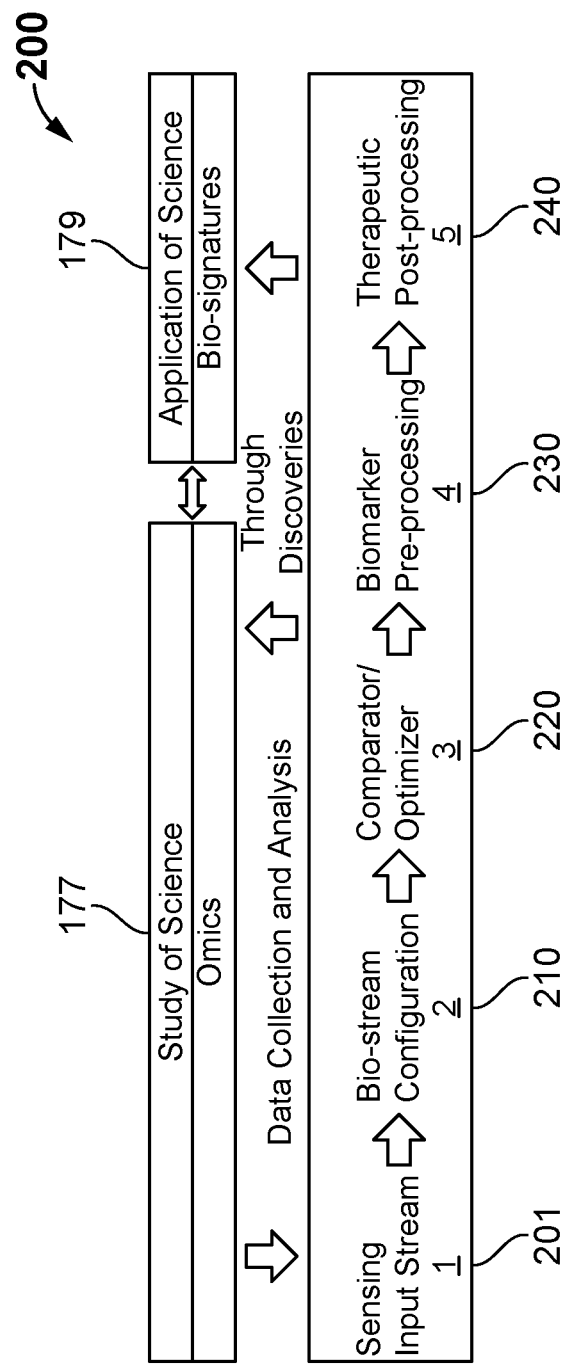
FIG. 6B provides a general flow diagram of the generic steps in the omics to bio-signatures and therapeutic processing of the system.

FIG. 6B describes how the omics 177 interact with the information flow through the system 200. The omics 177 feed data into the system 200, which performs data collection and analysis of the information as it collects after processing. The omics 177 feed data into the sensing input stream 201, which passes the data to the bio-stream configuration 210, then to the comparator/optimizer 220, which transfers the information to the biomarker pre-processing 230. The biomarker pre-processing 230 feeds the information to both omics 177 and the therapeutic post processing 240. After the therapeutic post processing the data is transferred to bio-signatures 179. Omics 177 and bio-signatures 179 bi-directionally share the study of science 177 and the application of science 179 as data discoveries based on the analyzed data from the system 200. As bio-signatures 179 data feeds Omics 177, the loop continues resulting in refinement of the information detected, predicted biomarkers concluded and bio-signatures applied.

Figure 6C:
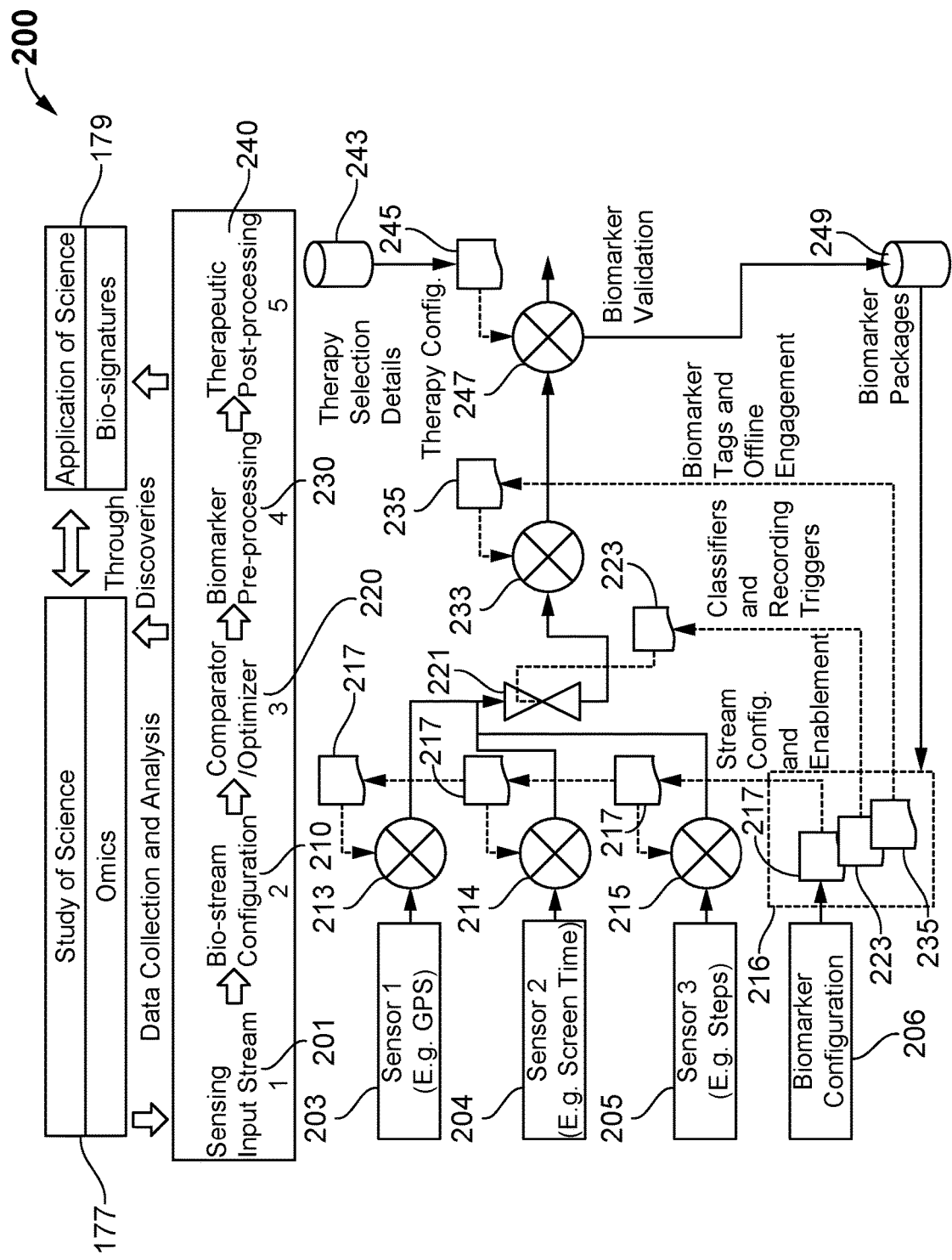
FIG. 6C provides a detailed flow diagram which depicts the information flow and configuration file flow for biosignature and therapeutic processing.

FIG. 6C describes the information flow through the system 200 with inputs from omics 177 and outputs to biosignatures 179. From left to right, there are multiple sensors which could exist on either a mobile client or a server. Information flows through the system in five distinct parts: sensing input stream 201, bio-stream configuration 210, comparator/optimizer 220, biomarker pre-processing 230, and therapeutic post processing 240. The derivation of them means that the sensor data would be consumed through the stream configuration 210, followed by the comparator/optimizer 220, followed by the biomarker pre-processing 230, and finally the therapeutic post-processing 240. Each stage after the raw sensor input stream 201 includes the use of a configuration file to modify and adjust for optimal data collection through the system. The configuration files decide what is able to be defined, how measurements from sensors are captured, how they are recorded, and whether they are pulled or listened to. This is defined through duty cycle-on/off capability, to say sensor is disabled and enable at specific specificity, when on degree of sampling taken and accuracy perspective, the ability of sensors to collect and process data, ex. GPS high level accuracy vs. low level. The system has different levels of configuration file to define on/off duty cycle time, accuracy needs, priority, and filters that are specific to controls on different mobile platforms.

Sensing Input Stream

Sensing input stream 201 includes raw data from sensor "1" 203, sensor "2" 204, sensor "3" 205, and the biomarker configuration 206. Each biomarker configuration 206 is a package 216 that combines a stream configuration file 217, a classifier and recording triggers configuration file 223, and a biomarker tags configuration file 235 for detecting in an offline engagement. The sensor information may include varying data sources like GPS data, screen time, an individual's steps, etc. Once the raw data is observed the information is sent to the stream configuration 210.

Stream Configuration

Figure 7:
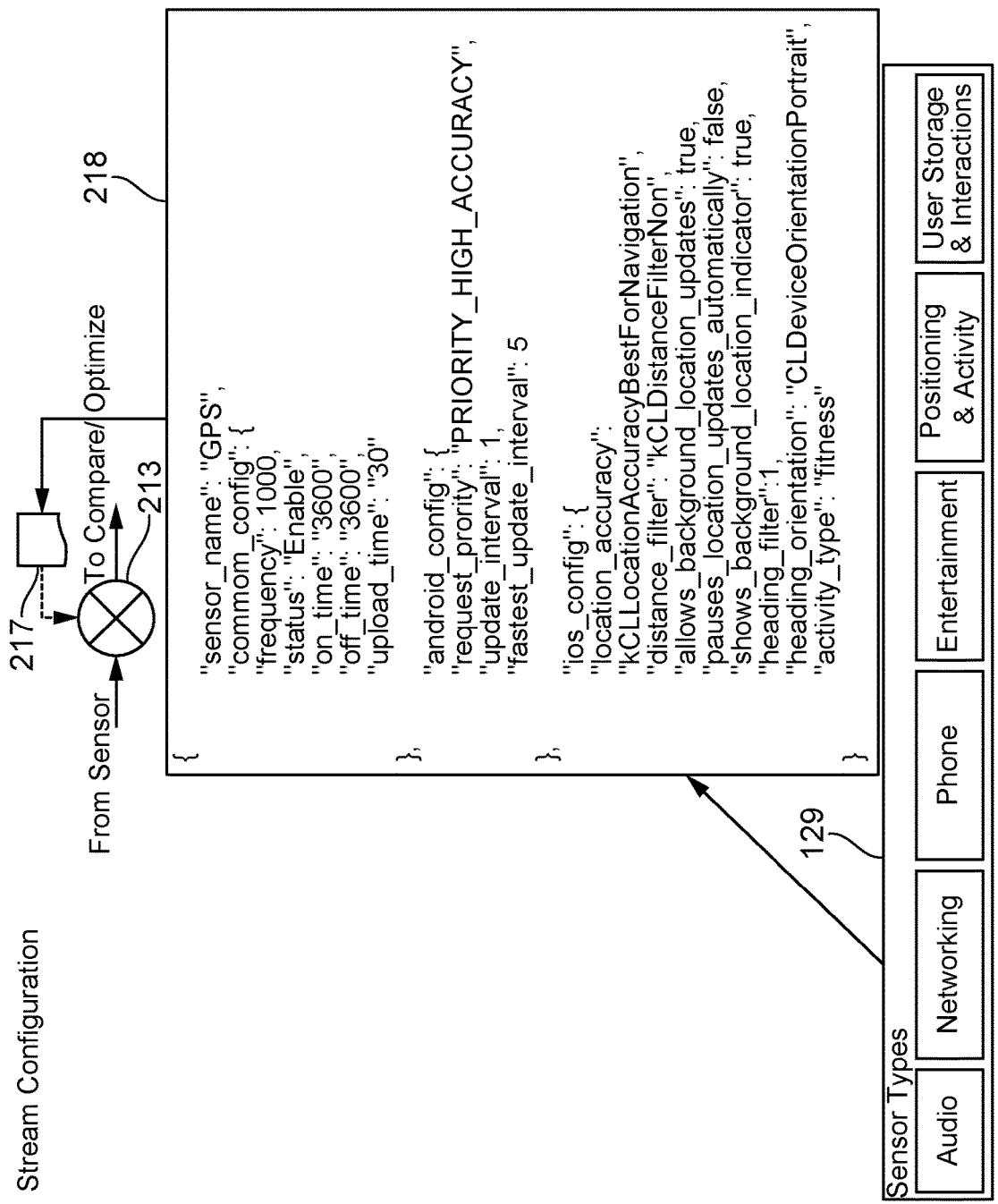
FIG. 7 depicts the stream configuration of the present invention.

Based on these inputs for the stream configuration 210, FIGS. 6 and 7, would modify the sensors 203, 204, 205 based on the needs required by the comparator/optimizer stage 220 to assess the sampled data. If low accuracy and low sampling is required, this would be specified by the stream configuration file 217. Sensor "1" 203 data is processed by stream configurator 213, sensor "2" 204 data is processed in stream configurator 214, sensor "3" 205 data is processed in stream configurator 215. Biomarker stream configuration file 217 feeds back into the stream configurators 213, 214, 215 and refines what information is obtained from each sensor 203, 204, 205. As depicted in FIG. 7, a sample of a stream definition 218 defined with stream configuration file 217 creates a layer of flexibility in how sensor features/type 129 are: captured, recorded, polled, and listened to through the duty cycle, sampling and controls.

The system 200 can support multiple stream configuration files 210 as they are tied to the rules required for the biomarker configuration 206. Multiple biomarkers 206 may require multiple streams, in cases where there are multiple needs for the same stream, the highest precision during the specific time domain wins.

Comparator/Optimizer

As seen in FIG. 6A-FIG. 8, the comparator/optimizer section 220 which modifies the recording of the sensing input streams 201 through the stream configurator 213, 214, 215 based on rules defined in the classifier and recording trigger configuration file 223. The stream configuration 213, 214, 215 flows into comparator/optimizer 221 that has classifiers and record triggers. Data from the comparator/optimizer 221 goes to preprocessing/biomarker tagging 233, where the biomarkers are a combination of different sensing events derived from the comparator/optimizer 221. Each data pathway into and out of the comparator/optimizer grows in bandwidth and shrinks in bandwidth, depending on needs of the system, while each pathway continues to be further optimized. This optimizes predictability, accuracy needs, reduction of false positives, total system and client level processing time, battery life, and overall efficiency of the whole system at each gate through the network.

The classifier and recording triggers biomarker configuration file 223 can indicate many types of classifiers, rules, recording events handled by the incoming streams from stream configurators 213, 214, and 215. For example, if there is a location classifier, for instance that describes the location as a library, church, school or restaurant; this could be based on the precision reporting of a sensor like Sensor "1" 203 collected through the biostream of stream configurator 213. Alternate sensors could be IP location identification, RF/RSSI proximity and triangulation between wireless sources like Wi-Fi or Bluetooth or Cell towers, or postal address identification.

The comparator/optimizer 221 is rules-based and will enable, disable, or change configurations to higher or lower accuracy as needed. The comparator/optimizer 221 can be a condition optimizer and a queue comparator. The rules by default may enable sensor "1" 203 through stream configurator 213, if a specific behavior occurs, the rules then enable sensor "2" 204 through stream configurator 214, and if an additional behavior occurs, sensor "3" is enabled through stream configurator 215. Note that each sensor can have multiple signals within it. Signal 1 (SIG1) 227 relates to a client device or phone being connected to or on the charger and when SIG1 227 is received by the comparator/optimizer 221 it is compared to a set of rules 224, to determine which sensor to enable or disable. For example, the comparator may have a set of three rules (Rule 1 or R1, Rule 2 or R2, and Rule 3 or R3) which make up the set of rules 224 defined within the classifier and recording triggers configuration file 223. R1 may be related to the client device or phone being on the charger and what signal to record and classifier while influencing subsequent rules, R2 may be related to the recording trigger of the phone being removed from the charger and the signal related to utilize or adjust, and R3 may deal with the screen on detected time to trigger the GPS location of the phone and subsequent triggers and recording configurations required as result. In this case, the comparator/optimizer is interested in detecting when the user is not charging their phone, actively using the phone and their precise location at the time of use.

Figure 8:
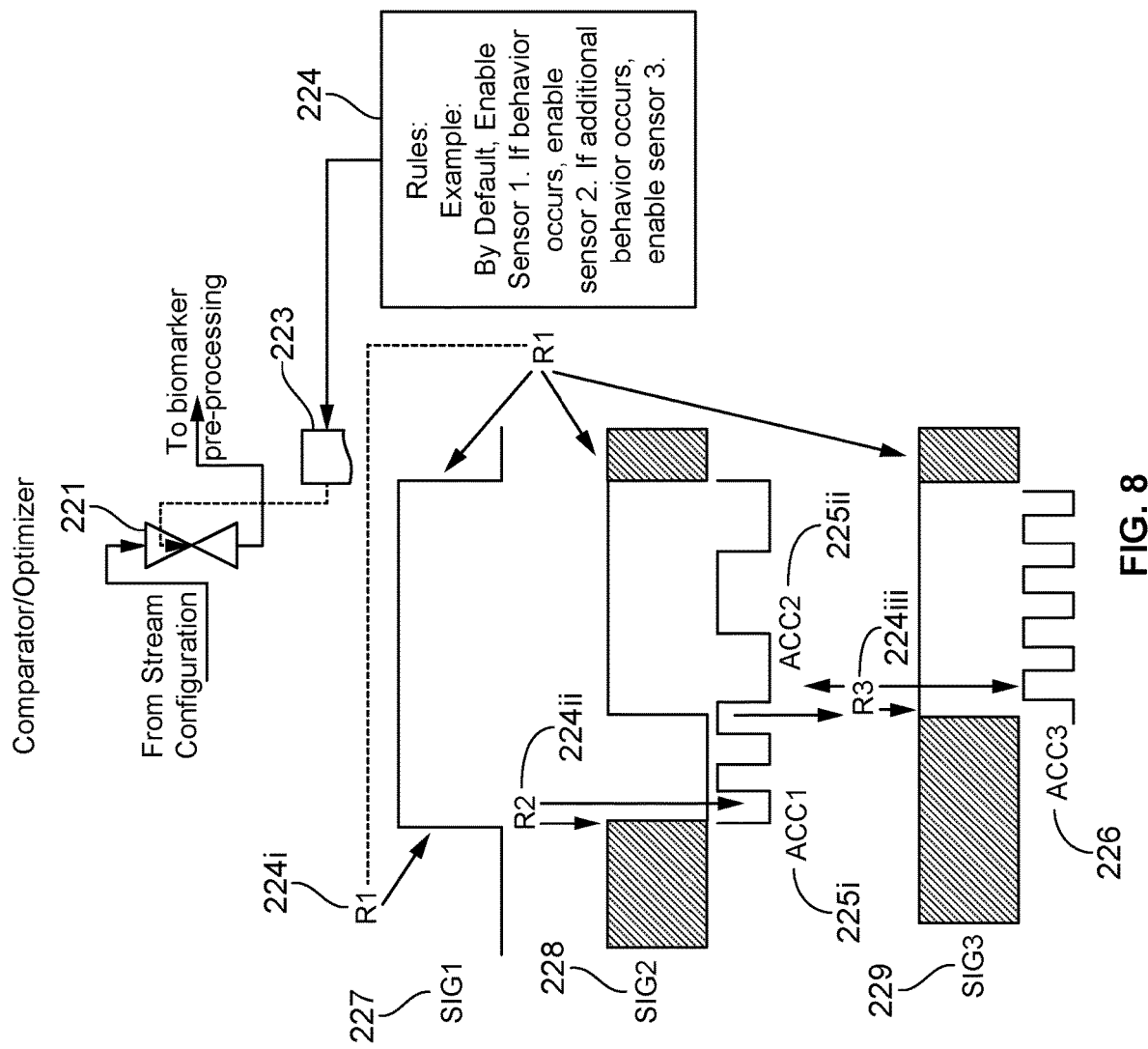
FIG. 8 depicts the comparator/optimizer configuration of the present invention.

As seen in FIG. 8, Signal 1 (SIG1) 227 is monitored through R1 224$i$ regardless of when the phone is on the charger, so the comparator/optimizer 221 is receiving the battery sensor SIG1 227 from the device. When the rise-time of the charge state changes (indicating the phone is removed from the charger), then R1 224$i$ enacts R2 224$ii$ and the comparator/optimizer enables screen time sensor Signal 2 (SIG2) 228 at an accuracy level 1 (ACC1) 225$i$. The ACC1 225$i$ has a high accuracy because the system is searching for the state transition of the screen from SIG2 being turned on by the user. When the rise-time of the screen state changes (indicating the screen is turned on), then R2 224$ii$ enacts R3 224$iii$ and the comparator/optimizer enables GPS location Signal 3 (SIG3) 229 at an accuracy level 3 (ACC3) 226. When R3 224$iii$ is met, there would be a corresponding change from ACC1 225$i$ for SIG2 228 to accuracy level 2 (ACC2) 225$ii$. ACC2 225$ii$, for example, could be a lower accuracy level that uses less battery life in detecting screen off time. If the fall-time of the charge state changes by monitoring SIG1 227 (indicating the phone is place back on the charger), then R1 224$i$ redacts both R2 224$ii$ and R3 224$iii$ and further disables SIG2 228 and SIG3 229 in this situation. Or, as another conditional rule for example, if battery life starts to deplete below a threshold level, certain additional rules can be implemented to turn off the client device to save on power as part of graceful degradation of service.

Another example, instead of only collecting screen time, if enough steps are collected that the data suggests that the individual has walked outside of the building, and they have turned on the mobile screen (suggesting they are looking for a new destination or that they have left a social environment and want to check messages), then the GPS can turn back on as a method of confirmation. The sudden movement combined by the threshold, plus the screen enables the location sensor to see if they have left the environment or entered a new environment. A sudden reduction in movement, plus the screen disabled could also enable another sensor such as linear acceleration to help detect whether the individual is now driving. This added signal for steps demonstrates a case where false positives can be further reduced to define the output of the comparator/optimizer that is feeding the biomarker pre-processing predictor. By allowing the configuration files to be modified during run-time of the application, the system can adaptively change the biostream configurations and the signal detection mechanisms that provide a higher level of usefulness to the biomarker and therapeutics, and overall the bio-signatures of individuals and these scenarios.

Figure 9:
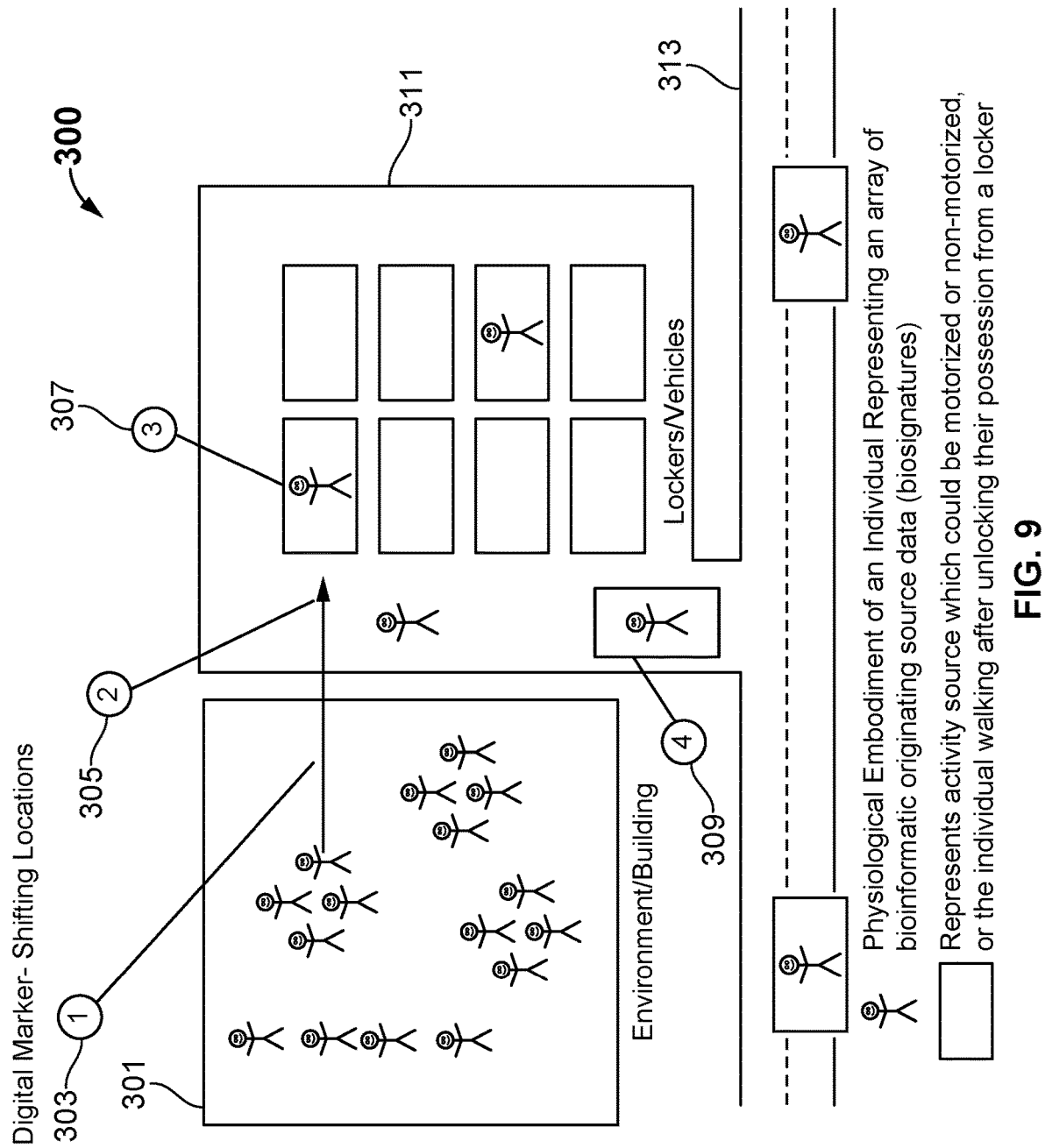
FIG. 9 depicts a digital marker analysis example.
Figure 10:
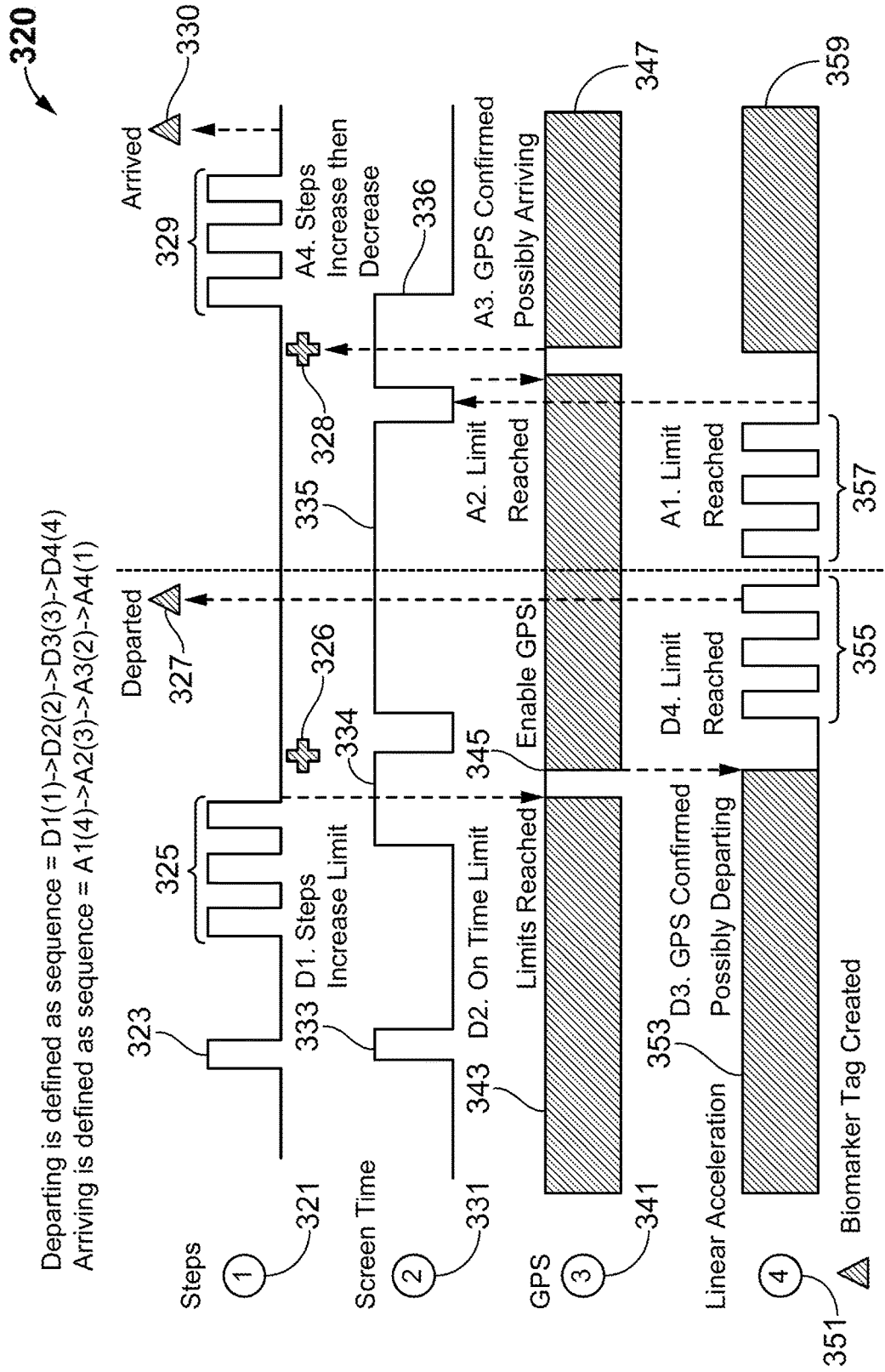
FIG. 10 depicts an example of the signal stream showing biomarker tag creation with sensor stream adjustment and activation or deactivation.

FIGS. 9 and 10 provide a graphical example, where an individual is in a typical environment including the changing relative proximity to other physiological embodiments representative of individuals and departs and/or arrives with shifting or varying locations that encompass a degree of individuals from a social representation and changing interactions or activities which can assist in inferring social acceptance, social avoidances and psychosocial and behavioral impacts of such scenarios. Some sensors are always required, some with different sampling rates, and some are not required so they are minimally turned on and off as required.

In FIG. 9, a user is in an environment/building 301 surrounded by a degree of other personas/individuals and (1) steps are taken 303 which show that the user has left the environment/building 301 such as a school, workplace, bar, or users' home. As the user leaves, (2) the screen associated with the user's device (e.g., mobile phone) is turned on, or if the user is a arriving, the phone's screen may be turned off 305. The GPS detection 307 (3) may be activated to verify and possibly classify where the user is arriving from or leaving from. For this example, the user's GPS detection 307 indicates the user is approaching a destination, such as their vehicle or a locker 311 and the detection unit 307 tracks the user as their linear acceleration is triggered. For example, when the user's linear acceleration 309 (4) indicates the user's device (and the user) is walking or moving, such as in a vehicle or on a bike. The GPS detection sensor or GPS unit 307 will continue to collect data as the user is (4) moving such as driving, walking or riding on a roadway, footpath, bike path, or train tracks 313. Appreciate, the system is designed to track and determine bio-informational data on many individual users and therefore, multiple users are depicted in FIG. 9. The stick figures, in FIG. 9, represent the physiological embodiment of an individual, or individuals, which represents an array of bioinformatic originating data collectively (e.g., biosignature data or biosignatures). The array of blocks 311 represent an activity source which could be a motorized vehicle (e.g., car) or a non-motorized vehicle (e.g., bicycle), or the individual could be walking.

FIG. 10 depicts the user arriving or departing a location while showing the different sensors being activated along the time of arrival or departure. Departure is defined as sequence=D1(1)→D2(2)→D3(3)→D4(4). Arriving is defined as a sequence=A1(4)→A2(3)→A3(2)→A4(1). Signal 1 321 is the steps the user takes and may be reported by the phone or by a wearable sensor such as a watch, signal 2

331 is the screen time of the user device and is reported by the phone, signal 3 341 is the GPS or location and can be either the phone or a location tag, or badge worn by the user or in proximity to the user, and signal 4 351 is linear acceleration and can be either the phone, a wearable device such as a watch or a sensor within the car. As the user is preparing to depart signal 1 steps 321 and signal 2 screen time 331 are activated, while signal 3 GPS 341 and signal 4 linear acceleration 351 are disabled by the comparator/optimizer sensor stream 343 and 353. The user is going in a slow pace or a limited number of steps within a specified duration 323 perhaps getting their coat or using the restroom and is looking at their device for a short duration 333 perhaps looking at the time in preparation to leave. The user increases the pace or number of steps increases to a specified limit within a specified duration 325, the screen of the device is activated for longer duration 334, and limits are reached suggesting that user is shifting locations as potential predictive digital marker/biomarker that cause the comparator/optimizer to enable GPS 345 and once the GPS reaffirms possible departure by stopping the biostream of Signal 1 for steps 321 while enabling the biostream of Signal 4 for the linear accelerator 351. When GPS 341 is enabled 345, the sampling frequency is adjusted for a change in sensor stream 326 to reduce accuracy needs and save battery, network utilization, and processing commitment/cycles and commitment by reducing prioritization. The screen time becomes constant 335 as the user uses GPS on their phone. The linear accelerator is turned on as the departure limit is reached 355 and the system marks the user as departed 327 by validating the biomarker tag for the given therapeutic, e.g., leaving a support group for a cancer survivor individual. After the user is marked as departed, the arrival limit is reached 357, perhaps by slowing down for a given length of time, suggesting that the individual is no longer moving, and to reduce false positives, the screen on time is turning off periodically from Signal 2 for screen time 331 suggesting interactions from the user in a non-driving scenario. Signal 3 for GPS 341 is enabled momentarily to confirm location and predict a possible arrival of the user to a new location, and the sampling frequency is adjusted again for Signal 1 Steps 328. The comparator/optimizer disables GPS 347 after enabling higher accuracy and disables the linear accelerator 359 at the same time. Signal 2 for screen time 331 is observed as off for a specified duration in 336, and the steps increase then decrease at pace 329 indicating arrival 330 by validating the biomarker tag for the given therapeutic, e.g. arriving at a pub for a cancer survivor individual suggesting risk or relapse of an addictive dependency.

A key point of the digital marker data collection example in FIGS. 9 and 10, is that the accuracy of this system is improved, by the ability to remove false positives, by adjusting the configuration of the biostreams genetic makeup within the digital marker detection utilized by the biomarker and redefining rules, triggers and biostream configuration used for biomarker predictors and therapeutics.

Biomarker Preprocessing

FIG. 6 depicts the biomarker pre-processing 230, which treats the combination of sensors 203, 204, 205 as a tag based on specified limits assigned during stream configuration 210 and comparator/optimizer 220. Biomarker pre-processing 230 forms the basis for the biomarker tags configuration file 235. By managing a set of configurable biomarkers on the mobile device the data can latch specific conditions from the comparator/optimizer stage 220. The information from the comparator/optimizer 221 is processed by the biomarker pre-processor 233 with input from the biomarker tags and offline engagement configuration file 235.

Biomarker pre-processing 230 is defined by suggestive inputs stating conditions to represent signal interaction. Movement is suggested by sensors 129, like an accelerometer or steps depending on availability and their representative limits, with phone behavior suggested by Screen On/Off count within a specified percentage and usage behaviors compared, which result in the individual actively checking their phone. Biomarker predictor tags are applied to suggest an anxiety qualifier, which can later be counted on the server side for confirming. If more data is needed before reaching this, it would be handled by the comparator/optimizer, which could result in user instructions to take a blood pressure measurement for instance. It may also happen where additional sensors, and their biostream are not required to reduce false positive, and that in fact they can be omitted while generating the same results with or without. This allows the system to best control the needs of the sensor data based on the accuracy and provisioning of the validate biomarkers collected.

For instance, in the previous example, an individual walks a specified number of steps, combined with screen time, GPS and linear acceleration is considered as departed from a location. This marker when utilized in context of going to the gym and leaving the gym can be used to transparently collect a window of time that can be used in conjunction with other biomarkers as part of an overall therapeutic.

Let's say that collecting heart rate is needed at a high sampling rate from a wearable sensor that the individual is always wearing, and that the assessment of the heart rate as part of a workout occurs on the backend server when the user indicates they are at the gym. The ability to detect they are at the gym and the ability to correlate changing heart rates as a workout related effort, versus efforts by the individual in trying to catch a train or flight connection which can also impact heart rate are 2 very different things as to the impact and results observed. Thus, correlating these 2 events allows the system to develop personalized messages to the user in different scenarios while not requiring all of the system data all of the time. Biomarkers allow the smart detection of situations/scenarios to assist in personalized therapy.

One of the main functions of the application is to determine smartly what sensors need to collect data from doing which conditions that is should be forwarding for biomarker pre-processing. Biomarker pre-processing 131 data needs determine which sensors are used and effects the rules to limit the information coming in. Preprocessing forms a basis for biomarker tagging/feature classification. Pre-processing helps with overall therapeutics indexes on the back-end server side, latches specific conditions from comparator/optimizer stage to help determine which data to process. For example, an individual showing different patterns of sensors that a user is actively checking a phone needs 3 things: (1) individual present (need a way to tell), (2) user actively moving (pacing)/not moving, and (3) what is current state of phone—i.e. plugged in or audible or visual sensor. The pre-processing tags define suggested inputs related to signal interaction, and their limits to suggest qualifiers to be forwarded for confirmation, to reduce the number of false positives. If more data is still required, the system has the ability to notify a user device that more sensors are needed, or the user needs to do an external act (e.g., check blood pressure, can eventually turn off a requirement). One or more biostream or sensor configuration files, for determining which sensors are on & off, sampling frequency, and other configuration attributes, are resident on the client device. The preprocessing may be handled on both the client side, and the server side, or a combination of both. A feedback loop can be implemented to reduce false positives, by way of feedback loop driven by configuration files, across the data input stages.

Therapeutic Post Processing

FIG. 6 depicts the therapeutic post-processing 240 of the system of the present invention, which combines these smartly detected biomarkers into meaningful therapy use cases as personalized through the system and the individual during use or non-use of the system. The biomarkers are sent to the therapy post-processor 247 which forms biomarker packages 249. The biomarker packages feed back into the biomarker configuration files 217, 223, and 235. The therapy post-processor 247 also obtains information from the therapy configuration file 245 which is made by the therapy selection details 243.

The purpose of post-processing is to leverage the data lake of crowd-sourced information, and reduce the number of false positives, while applying new technique and insights to the data recorded. While doing so, it is very common that a feedback loop will send corrections back downstream to the mobile to further reduce false positives while continuously improving the data set collected across other participants. A learning system can be implemented which can learn and change rules, specificity, driver conditions, and pre-processing directives. The outcome will help determine the correct engagement message, therapeutics and user needs to help encourage opportunities and success.

The therapeutic plans can be discussed or defined as recipes. As in the earlier example of cancer survivorship, a biomarker may require other biomarkers in order to be detected, such as detecting whether a cognitive test has started or stopped, or that the arrival to or departure from a community location has occurred. Each therapeutic plan defines a set of biomarker packages and outcomes to measure and detect level of engagement, success and failure points. The prerequisites for each biomarker recipe has its own mandatory needs that must be met in order to properly detect a given biomarker of the therapy class. Within each biomarker itself is a subset of configurations required to define the above input streams informational flow through the client.

By way of example, a recipe based on the example from FIG. 5 may have additional prerequisites defined. These additional prerequisites would be utilized by the system to help determine when the biomarkers are active and to help reduce false positives. Additional prerequisites can be added and updated at any time to continue to reduce and improve the communication and detection components of the system. Additional prerequisites can also be added for optimization and stream configurations based on biomarkers that share biostreams during detection to override settings when both biomarkers are in use. There may be off use times like when the individual is asleep, where biostreams may not conflict for all biomarkers.

Tailored Application

As previously described above, the system of the present invention can identify recipient bioinformatic data to generate biomarker data and biosignature profiles. The use of the biomarker and biosignature data and profiles can be used by the system to create a myriad of therapeutic plans as well as configure the application to provide tailored health modules and features. The features of the application as a whole and the features of the health modules within the application can be tailored or activated/deactivated. By varying the application, modules, and the application of the recipient's therapeutic plan or plans, the system can create a vast number (tens of thousands) of configurations of the application, the modules, and plans. The result is the present invention is able to provide a tailored health or therapeutic application, with therapeutic modules and therapeutic plans all designed or configured to the recipient's biomarker and biosignature data and profile. Thus, the system provides significant flexibility and customizability through use of modules, activated features, configuration profiles and managers. Further, the operations of the program or modules enables or customizes interaction with the user according to the user's current context, behavior, medical history, history of interactions with the program, and other user data.

The application, modules within the application, the therapeutic plans, and the biostream configurations (collectively the "therapeutic array) can be designed to operate independently of other applications or programs on the device and independent of other therapeutic arrays so that operation or delay of any therapeutic array or other program does not block operation of the other arrays.

The system of the present invention can be very effective at addressing complex scenarios where users experience diverse and changing needs over time or where users have demanding needs. An example is treating and tracking the effectiveness of modern cancer treatments during treatment and when cancer is in remission. In many instances, cancer patients and cancer survivors are provided care plans to address health and other challenges often faced during or after cancer treatment. Using the present invention, the system is able to provide tailored therapeutic plans specific to the bioinformatic data of the patient or device user.

Cancer is an ideal example to highlight the scale and flexibility of the system, because cancer and the related treatments generally have systemic effects rather than primarily localized effects on the body. Such symptoms often come in clusters that are seemingly unrelated to the portions of the body where the cancer is located. For example, after treatment for throat cancer, patients may experience a wide range of secondary symptoms or notice an impact across many aspects of their lifestyle. Such symptoms or impacts may include changes to sleep patterns, eating habits, activity levels, anxiety levels, pain levels in various different locations of the body, and so on.

In addition, chemotherapy and medication, drugs or other treatments may have side effects or complications such as neuropathy. The symptoms experienced are highly variable from one patient to the next, and often, the symptoms cannot be accurately predicted. In addition, the time the symptoms appear and the intensity of the symptoms vary. As a result, typical care plans for cancer patients and cancer survivors are often inadequate to address the individualized and varying needs of specific patients. Therefore, the system of the present invention can be used to provide individualized therapeutic plans through an individualized therapeutic application. The therapeutic modules within the application can be added or modified as treatments are added or changed, as symptoms appear or change, and as the recipients' bioinformatic data provides feedback on how the recipient is handling the treatment, medication, and therapeutic plans.

The system includes multiple digital therapeutics programs, or modules within an application, with each module capable of handling a different aspect of the user's needs. For example, different modules can address different aspects of physical, psychological, emotional, and social needs, and another module may have a corresponding set of instructions or rules which perform specific actions when appropriate thresholds or conditions are met. The system also tracks and uses the patient or user's responses to the therapeutic plans and the system can automatically adjust the features and functions of the modules and the therapeutic plan.

The systems and methods of the invention in described embodiments may be implemented as a system, method, apparatus or article of manufacture using programming and/or engineering techniques related to software, firmware, hardware, or any combination thereof. The described operations may be implemented as code maintained in a "computer readable medium", where a processor may read and execute the code from the computer readable medium. A computer readable medium may comprise media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. The code implementing the described operations may be further implemented in hardware logic (e.g., an integrated circuit chip, Programmable Gate Array (PGA), Application Specific Integrated Circuit (ASIC), etc.). Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a computer readable medium at the receiving and transmitting stations or devices. An "article of manufacture" comprises computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the present invention, and that the article of manufacture may comprise suitable information bearing medium known in the art.

In an embodiment of the invention, the systems and methods use networks, wherein the term, 'networks' means a system allowing interaction between two or more electronic devices and includes any form of inter/intra enterprise environment such as the world wide web, Local Area Network (LAN), Wide Area Network (WAN), Storage Area Network (SAN) or any form of Intranet.

In an embodiment of the invention, the systems and methods can be practiced using any electronic device. An electronic device, for the purpose of this invention, is selected from any device capable of processing or representing data to a recipient and user and providing access to a network or any system similar to the internet; wherein the electronic device may be selected from, but is not limited to, personal computers, mobile phones, laptops, palmtops, tablets, portable media players and personal digital assistants.

As noted above, the processing machine used to implement the invention may be a suitable computer or other processing machine. The processing machine may also utilize (or be in the form of) any of a wide variety of other technologies including a special purpose computer, a computer system including a microcomputer, mini-computer or mainframe for example, a programmed microprocessor, a micro-controller, a peripheral integrated circuit element, a CSIC (Consumer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing the steps of the processes of the invention.

The processing machine used to implement the invention may utilize a suitable operating system (OS). Thus, embodiments of the invention may include a processing machine running the Unix operating system, the Apple iOS operating system, the Linux operating system, the Xenix operating system, the IBM AIX™ operating system, the Hewlett-Packard UX™ operating system, the Novell Netware™ operating system, the Sun Microsystems Solaris™ operating system, the OS/2™ operating system, the BeOS™ operating system, the Macintosh operating system (such as macOS™), the Apache operating system, an OpenStep™ operating system, the Android™ operating system (and variations distributed by Samsung, HTC, Huawei, LG, Motorola, Google, Blackberry, among others), the Windows 10™ operating system, the Windows Phone operating system, the Windows 8™ operating system, Microsoft Windows' Vista™ operating system, the Microsoft Windows™ XP™ operating system, the Microsoft Windows™ NT™ operating system, the Windows™ 2000 operating system, or another operating system or platform.

The systems and methods of the invention may utilize non-operating systems (aka serverless architecture) as well for distributed processing. In the processing of the invention, services on cloud computing networks leveraging systems like AWS (as offered by Amazon Web Services, Inc.), BlueMix (as offered by IBM), and Microsoft Azure, can perform data collection services using varying technologies that are spun up on demand using tools like Chef to create container-based deployments like Docker, or non-container compute services (e.g., AWS Lambda).

The invention provides real-time analytics processing that requires scale on demand to the recipients and users in the system, in accordance with at least one embodiment of the invention. Such offerings as AWS lambda and Kinesis (as offered by Amazon Web Services, Inc.) are among those that may be used in implementation of the invention. For example, AWS Lambda may be utilized to execute code (to perform processes of the invention) in response to various triggers including data changes, shifts in system state, or particular action taken by recipients and users. Similarly, in an embodiment, the OS (operating system) of the invention might be encapsulated in an EC2 instance (as offered by Amazon Web Services, Inc.) or multiple instances for deployment.

It is appreciated that in order to practice the method of the invention as described above, it is not necessary that the processors and/or the memories of the processing machine be physically located in the same geographical place. That is, each of the processors and the memories used by the processing machine may be located in geographically distinct locations and connected, so as to communicate in any suitable manner, such as over a network or over multiple networks. Additionally, it is appreciated that each of the processor and/or the memory may be composed of different physical pieces of equipment. Accordingly, it is not necessary that the processor be one single piece of equipment in one location and that the memory be another single piece of equipment in another location. That is, it is contemplated that the processor may be two pieces of equipment in two different physical locations. The two distinct pieces of equipment may be connected in any suitable manner. Further, it is appreciated that processing units/processors can be physical processors, software, through a distributed service, or any combination of the three. Additionally, the memory may include two or more portions of memory in two or more physical locations.

To explain further, processing as described above is performed by various components and various memories. However, it is appreciated that the processing performed by two distinct components as described above may, in accordance with a further embodiment of the invention, be performed by a single component. Further, the processing performed by one distinct component as described above may be performed by two distinct components. In a similar manner, the memory storage performed by two distinct memory portions as described above may, in accordance with a further embodiment of the invention, be performed by a single memory portion. Further, the memory storage performed by one distinct memory portion as described above may be performed by two memory portions.

Further, as also described above, various technologies may be used to provide communication between the various processors and/or memories, as well as to allow the processors and/or the memories of the invention to communicate with any other entity, so as to obtain further instructions or to access and use remote memory stores, for example. Such technologies used to provide such communication might include a network, the Internet, Intranet, Extranet, LAN, an Ethernet, or any client server system that provides communication, for example. Such communications technologies may use any suitable protocol such as TCP/IP, UDP, or OSI, for example.

Further, multiple applications may be utilized to perform the various processing of the invention. Such multiple applications may be on the same network or adjacent networks, and split between non-cloud hardware, including local (on-premises) computing systems, and cloud computing resources, for example. Further, the systems and methods of the invention may use IPC (inter-process communication) style communication for module level communication. Various known IPC mechanisms may be utilized in the processing of the invention including, for example, shared memory (in which processes are provided access to the same memory block in conjunction with creating a buffer, which is shared, for the processes to communicate with each other), data records accessible by multiple processes at one time, and message passing (that allows applications to communicate using message queues).

As described above, a set of instructions is used in the processing of the invention. The set of instructions may be in the form of a program or software. The software may be in the form of system software or application software, for example. The software might also be in the form of a collection of separate programs, a program module within a larger program, or a portion of a program module, for example. The software used might also include modular programming in the form of object-oriented programming. The software tells the processing machine what to do with the data being processed.

Further, it is appreciated that the instructions or set of instructions used in the implementation and operation of the invention may be in a suitable form, such that the processing machine may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processing machine, i.e., to a particular type of computer, for example. The computer understands the machine language.

Any suitable programming language may be used in accordance with the various embodiments of the invention. Illustratively, the programming language used may include assembly language, Ada, APL, Basic, C, C++, C#, Objective C, COBOL, dBase, Forth, Fortran, Java, Modula-2, Node.JS, Pascal, Prolog, Python, REXX, Visual Basic, and/or JavaScript, for example. Further, it is not necessary that a single type of instruction or single programming language be utilized in conjunction with the operation of the system and method of the invention. Rather, any number of different programming languages may be utilized as is necessary or desirable.

Also, the instructions and/or data used in the practice of the invention may utilize any compression or encryption technique or algorithm, as may be desired. An encryption module might be used to encrypt data. Further, files or other data may be decrypted using a suitable decryption module, for example.

As described above, the invention may illustratively be embodied in the form of a processing machine, including a computer or computer system, for example, that includes at least one memory. It is to be appreciated that the set of instructions, i.e., the software for example that enables the computer operating system to perform the operations described above, may be contained on any of a wide variety of media or medium, as desired. Further, the data that is processed by the set of instructions might also be contained on any of a wide variety of media or medium. That is, the particular medium, i.e., the memory in the processing machine, utilized to hold the set of instructions and/or the data used in the invention may take on any of a variety of physical forms or transmissions, for example. Illustratively, as also described above, the medium may be in the form of paper, paper transparencies, a compact disk, a DVD, an integrated circuit, a hard disk, a floppy disk, an optical disk, a magnetic tape, a RAM, a ROM, a PROM, a EPROM, a wire, a cable, a fiber, communications channel, a satellite transmissions or other remote transmission, as well as any other medium or source of data that may be read by the processors of the invention.

Further, the memory or memories used in the processing machine that implements the invention may be in any of a wide variety of forms to allow the memory to hold instructions, data, or other information, as is desired. Thus, the memory might be in the form of a database to hold data. The database might use any desired arrangement of files such as a flat file arrangement or a relational database arrangement, for example.

In the system and method of the invention, a variety of "recipient interfaces" or "user interfaces" may be utilized to allow a recipient or user to interface with the processing machine or machines that are used to implement the invention. As used herein, a recipient or user interface includes any hardware, software, or combination of hardware and software used by the processing machine that allows a recipient or user to interact with the processing machine. A recipient or user interface may be in the form of a dialogue screen for example. A recipient or user interface may also include any of the following: a mouse, touch screen, keyboard, voice reader, voice recognizer, dialogue screen, menu box, list, checkbox, toggle switch, a pushbutton, or any other device that allows a recipient or user to receive information regarding the operation of the processing machine as it processes a set of instructions and/or provide the processing machine with information. Accordingly, the recipient or user interface is any device that provides communication between a recipient or user and a processing machine. The information provided by the recipient or user to the processing machine through the recipient or user interface may be in the form of a command, a selection of data, or some other input, for example.

As discussed above, a recipient or user interface is utilized by the processing machine that performs a set of instructions such that the processing machine processes data for a recipient or user. The recipient or user interface is typically used by the processing machine for interacting with a recipient or user either to convey information or receive information from the recipient or user. However, it should be appreciated that in accordance with some embodiments of the system and method of the invention, it is not necessary that a human recipient or user interact with a recipient or user interface used by the processing machine of the invention. Rather, it is also contemplated that the recipient or user interface of the invention might interact, i.e., convey and receive information, with another processing machine, rather than a human recipient or user. Accordingly, the other processing machine might be characterized as a recipient or user. Further, it is contemplated that a recipient or user interface utilized in the system and method of the invention may interact partially with another processing machine or processing machines, while also interacting partially with a human recipient or user.

What is claimed is:

1. A system of networked devices configured to provide adaptive therapeutic plans, the system comprising:
    a client device; and
    a server that includes memory storing a set of server instructions that, when executed by the server, configure the server to:
        receive input from a user of an application resident on the client device;
        select a therapeutic plan based on the input from the user; and
        transmit the selected therapeutic plan to the client device, wherein the therapeutic plan indicates a marker to be detected;
    wherein the client device that includes memory storing a set of client instructions that, when executed by the client device, configure the client device to perform operations comprising:
        storing a plurality of configuration profiles that specify different configurations for one or more sensors that can be used to acquire different types of data, the plurality of configuration profiles including profiles in which different combinations of sensors are active and in which different amounts of power are consumed, wherein the configuration profiles respectively specify configurations designed to acquire data to detect different markers;
        updating the application on the client device with the therapeutic plan;
        selecting a configuration profile from the plurality of configuration profiles stored by the client device, wherein the configuration profile is selected based on the marker indicated by the therapeutic plan, wherein the configuration profile indicates a configuration for one or more sensors to acquire data for detection of the marker, wherein the plurality of configuration profiles includes configuration profiles that respectively include different settings for the one or more sensors;
        adjusting operation of a sensor based on the selected configuration profile, wherein the sensor is a sensor of (i) the client device or (ii) a device in communication with the client device;
        after adjusting the operation of the sensor, receiving sensor data generated by the sensor with the sensor operating as specified by the selected configuration profile;
        evaluating the sensor data to determine whether the marker indicated by the therapeutic plan is present, wherein evaluating the sensor data comprises determining, based on the sensor data, whether a pattern indicative of a user activity or behavior has occurred; and
        adapting the therapeutic plan based on the determination whether the marker is present by modifying the therapeutic plan to obtain a personalized therapeutic plan for the user.

2. The system of claim 1, wherein the client device is configured to perform bi-directional communication with a plurality of data sources.

3. The system of claim 1, wherein adjusting the operation of the sensor comprises activating the sensor.

4. The system of claim 1, wherein the client device is configured to selectively obtain data from a plurality of data sources, wherein the plurality of data sources comprises at least one of a directly observed data source, a passively observed data source, an indirectly observed data source, a publicly observed data source, or a comparatively observed data source.

5. A method for adapting a therapeutic plan on a client device, the method comprising:
    receiving, by a server, input from the client device of a user of a therapeutic application resident on the client device;
    selecting, by the server, a therapeutic plan based on the input received from the client device;
    transmitting, by the server, the selected therapeutic plan to the client device, wherein the therapeutic plan indicates a marker to be detected;
    receiving, by the client device, the therapeutic plan;
    storing, by the client device, a plurality of configuration profiles that specify different configurations for one or more sensors that can be used to acquire different types of data, the plurality of configuration profiles including profiles in which different combinations of sensors are active and in which different amounts of power are consumed, wherein the configuration profiles respectively specify configurations designed to acquire data to detect different markers;
    updating the therapeutic application resident on the client device with the therapeutic plan;
    selecting a configuration profile from the plurality of configuration profiles stored by the client device, wherein the configuration profiles respectively specify different sensor configurations to each detect one or more markers corresponding to the configuration profiles, wherein the configuration profile is selected based on the marker indicated by the therapeutic plan, and wherein the configuration profile indicates a configuration for one or more sensors to acquire data for detection of the marker indicated by the therapeutic plan;

adjusting operation of a sensor based on the selected configuration profile, wherein the sensor is a sensor of (i) the client device or (ii) a device in communication with the client device;

after adjusting the operation of the sensor, receiving sensor data generated by the sensor with the sensor operating as specified by the selected configuration profile;

evaluating the sensor data to determine whether the marker indicated by the therapeutic plan is present; and adapting, by the client device, the therapeutic plan based on the determination whether the marker is present to obtain a personalized therapeutic plan for the user.

6. The method of claim 5, comprising performing, by the client device, bi-directional communication with a plurality of data sources.

7. The method of claim 5, wherein adjusting the operation of the sensor comprises activating the sensor.

8. The method of claim 5, wherein the client device is configured to selectively obtain data from a plurality of data sources, wherein the plurality of data sources comprises at least one of a directly observed data source, a passively observed data source, an indirectly observed data source, a publicly observed data source, or a comparatively observed data source.

9. A method performed by one or more computing devices, the method comprising:

storing, by the one or more computing devices, a plurality of configuration profiles that specify different configurations for one or more sensors that can be used to acquire different types of data, the plurality of configuration profiles including profiles in which different combinations of sensors are active and in which different amounts of power are consumed, wherein the configuration profiles respectively specify configurations designed to acquire data to detect different markers;

receiving, by the one or more computing devices, a therapeutic plan transmitted over a communication network, the therapeutic plan indicating a marker to be detected;

selecting, by the one or more computing devices, a configuration profile from the plurality of configuration profiles stored by the one or more computing devices, wherein the configuration profile is selected based on the marker indicated by the received therapeutic plan, and wherein the selected configuration profile indicates a configuration for one or more sensors to acquire data for detection of the marker;

adjusting, by the one or more computing devices, operation of a sensor based on the selected configuration profile, wherein the sensor is a sensor of (i) the one or more computing devices or (ii) a device in communication with the one or more computing devices;

after adjusting the operation of the sensor, receiving, by the one or more computing devices, sensor data generated by the sensor with the sensor operating as specified by the selected configuration profile;

evaluating, by the one or more computing devices, the sensor data to determine whether the marker indicated by the therapeutic plan is present; and adapting, by the one or more computing devices, the therapeutic plan based on the determination whether the marker is present to obtain a personalized therapeutic plan.

10. The method of claim 9, wherein the one or more computing devices are a single computing device.

11. The method of claim 9, wherein adjusting the operation of the sensor comprises activating the sensor.

12. The method of claim 9, wherein the sensor is configured to produce data indicating a physiological measurement, a location measurement, an activity measurement, an audio measurement, or an environmental measurement.

13. The method of claim 9, wherein the marker represents the occurrence of each of multiple different events or conditions in a predetermined sequence; and wherein the method includes detecting occurrence of the marker based on determining that each of multiple different events or conditions have been sensed in the predetermined sequence, wherein one or more of the multiple different events or conditions are indicated by the sensor data received from the sensor as adjusted according to the selected configuration profile.

14. The method of claim 13, wherein the events or conditions are actions of a user or conditions indicative of actions of the user.

15. The method of claim 13, wherein adjusting the operation of the sensor is performed in response to detecting at least one of the multiple different events or conditions.

16. The method of claim 13, wherein the method includes making adjustments to the operation of the sensor at different times through the occurrence of the predetermined sequence of events and conditions in order to detect the marker.

17. The method of claim 9, comprising:

determining that measurement data for a second sensor satisfies one or more criteria; and wherein adjusting operation of the sensor based on the selected configuration profile is performed in response to determining that the measurement data for the second sensor satisfies the one or more criteria.

18. The method of claim 9, wherein the selected configuration profile specifies multiple data collection actions and a configuration change between the data collection actions in order to detect the marker.

19. The method of claim 9, wherein the therapy plan indicates multiple markers to be detected;

wherein the method comprises:

selecting multiple configuration profiles that each correspond to one of the multiple markers, wherein each of the multiple configuration profiles indicates a configuration of the one or more sensors to acquire data for detection of the corresponding marker; and determining a configuration of the one or more sensors to use during a time period based on each of the selected multiple configuration profiles; and wherein adjusting the sensor comprises adjusting the sensor based on the determined configuration.

20. The method of claim 9, wherein the plurality of configuration profiles includes configuration profiles that are respectively configured to detect different markers using different combinations of sensors.

21. The method of claim 9, wherein evaluating the sensor data comprises:

assigning, based on the received sensor data, one or more tags indicating activities of a user or a state of the one or more computing devices; and determining whether the marker indicated by the therapeutic plan is present based on the assigned one or more tags.

22. The method of claim 9, wherein the selected configuration profile for the marker has a set of associated rules that specify (i) conditions for selectively activating each of multiple different sensors and (ii) portions of data from the multiple sensors to record;
    wherein adjusting the operation of the sensor comprises activating the sensor based on determining that a condition specified by the rules is present; and
    wherein the method includes recording a subset of data produced by the activated sensor based on the rules.

23. The method of claim 9, wherein the marker is an indicator of a susceptibility to or resilience to the development of a health condition.

24. The method of claim 9, wherein the plurality of configuration profiles includes configuration profiles that respectively specify configurations of the one or more sensors that consume different amounts of power.

25. The method of claim 9, wherein the plurality of configuration profiles includes configuration profiles for configurations that respectively collect a particular type of data at different levels of precision and that consume different levels of power to collect the particular type of data.

26. One or more non-transitory computer-readable media storing instructions that, when executed by one or more computing devices, cause the one or more computing devices to perform operations comprising:
    storing, by the one or more computing devices, a plurality of configuration profiles that specify different configurations for one or more sensors that can be used to acquire different types of data, the plurality of configuration profiles including profiles in which different combinations of sensors are active and in which different amounts of power are consumed, wherein the configuration profiles respectively specify configurations designed to acquire data to detect different markers;
    receiving, by the one or more computing devices, a therapeutic plan transmitted over a communication network, the therapeutic plan indicating a marker to be detected;
    selecting, by the one or more computing devices, a configuration profile from the plurality of configuration profiles stored by the one or more computing devices, wherein the configuration profile is selected based on the marker indicated by the received therapeutic plan, and wherein the selected configuration profile indicates a configuration for one or more sensors to acquire data for detection of the marker;
    adjusting, by the one or more computing devices, operation of a sensor based on the selected configuration profile, wherein the sensor is a sensor of (i) the one or more computing devices or (ii) a device in communication with the one or more computing devices;
    after adjusting the operation of the sensor, receiving, by the one or more computing devices, sensor data generated by the sensor with the sensor operating as specified by the selected configuration profile;
    evaluating, by the one or more computing devices, the sensor data to determine whether the marker indicated by the therapeutic plan is present; and
    adapting, by the one or more computing devices, the therapeutic plan based on the determination whether the marker is present to obtain a personalized therapeutic plan.

27. The one or more non-transitory computer-readable media of claim 26, wherein the one or more computing devices are a single computing device.

28. The one or more non-transitory computer-readable media of claim 26, wherein adjusting the operation of the sensor comprises activating the sensor.

29. A system comprising:
  one or more computing devices; and
  one or more non-transitory computer-readable media storing instructions that, when executed by the one or more computing devices, cause the one or more computing devices to perform operations comprising:
    storing, by the one or more computing devices, a plurality of configuration profiles that specify different configurations for one or more sensors that can be used to acquire different types of data, the plurality of configuration profiles including profiles in which different combinations of sensors are active and in which different amounts of power are consumed, wherein the configuration profiles respectively specify configurations designed to acquire data to detect different markers;
    receiving, by the one or more computing devices, a therapeutic plan transmitted over a communication network, the therapeutic plan indicating a marker to be detected;
    selecting, by the one or more computing devices, a configuration profile from the plurality of configuration profiles stored by the computing device, wherein the configuration profile is selected based on the marker indicated by the received therapeutic plan, and wherein the selected configuration profile indicates a configuration for one or more sensors to acquire data for detection of the marker;
    adjusting, by the one or more computing devices, operation of a sensor based on the selected configuration profile, wherein the sensor is a sensor of (i) the one or more computing devices or (ii) a device in communication with the one or more computing devices;
    after adjusting the operation of the sensor, receiving, by the one or more computing devices, sensor data generated by the sensor with the sensor operating as specified by the selected configuration profile;
    evaluating, by the one or more computing devices, the sensor data to determine whether the marker indicated by the therapeutic plan is present; and
    adapting, by the one or more computing devices, the therapeutic plan based on the determination whether the marker is present to obtain a personalized therapeutic plan.

30. The system of claim 29, wherein the one or more computing devices are a single computing device.

31. The system of claim 29, wherein adjusting the operation of the sensor comprises activating the sensor.

\* \* \* \* \*

UNITED STATES PATENT AND TRADEMARK OFFICE
CERTIFICATE OF CORRECTION

| | | |
|---|---|---|
| PATENT NO. | : 11,158,423 B2 | Page 1 of 1 |
| APPLICATION NO. | : 16/172346 | |
| DATED | : October 26, 2021 | |
| INVENTOR(S) | : Praduman Jain et al. | |

It is certified that error appears in the above-identified patent and that said Letters Patent is hereby corrected as shown below:

On the Title Page

Item [54], delete "ADAPTED" and insert -- ADAPTING --, therefor.

In the Specification

Column 1, Line 1, delete "ADAPTED" and insert -- ADAPTING --, therefor.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*